(12) United States Patent
Kaplan et al.

(10) Patent No.: US 8,764,796 B2
(45) Date of Patent: Jul. 1, 2014

(54) SUTURE METHOD

(75) Inventors: Andrew Kaplan, Hillsborough, NC (US); Gregory L Ruff, Chapel Hill, NC (US); Jeffrey C. Leung, Raleigh, NC (US); Matthew A. Megaro, Chapel Hill, NC (US)

(73) Assignee: Ethicon, Inc., Somerville, NJ (US)

( * ) Notice: Subject to any disclaimer, the term of this patent is extended or adjusted under 35 U.S.C. 154(b) by 1761 days.

(21) Appl. No.: 11/307,520

(22) Filed: Feb. 10, 2006

(65) Prior Publication Data

US 2006/0111734 A1    May 25, 2006

Related U.S. Application Data

(60) Division of application No. 10/065,256, filed on Sep. 30, 2002, now Pat. No. 7,056,331, which is a continuation-in-part of application No. 09/896,455, filed on Jun. 29, 2001, now Pat. No. 6,599,310.

(51) Int. Cl.
*A61B 17/04* (2006.01)

(52) U.S. Cl.
USPC .......................................... 606/228; 606/232

(58) Field of Classification Search
USPC .................................. 606/228, 232, 139, 151
See application file for complete search history.

(56) References Cited

U.S. PATENT DOCUMENTS

| | | | |
|---|---|---|---|
| 709,392 A | 9/1902 | Brown | |
| 733,723 A | 7/1903 | Lukens | |
| 789,401 A | 5/1905 | Acheson | |
| 816,026 A | 3/1906 | Meier | |
| 879,758 A | 2/1908 | Foster | |
| 1,142,510 A | 6/1915 | Engle | |
| 1,248,825 A | 12/1917 | Dederer | |
| 1,321,011 A | 11/1919 | Cottes | |
| 1,558,037 A | 10/1925 | Morton | |

(Continued)

FOREIGN PATENT DOCUMENTS

| BE | 1014364 | 9/2003 |
|---|---|---|
| CA | 2309844 | 12/1996 |

(Continued)

OTHER PUBLICATIONS

McKenzie, A.R.; "An Experimental Multiple Barbed Suture for the Long Flexor Tendons of the Palm and Fingers", The Journal of Bone and Joint Surgery, vol. 49B, No. 3, Aug. 1967, pp. 440-447.

(Continued)

*Primary Examiner* — Corrine M McDermott
*Assistant Examiner* — Alexander Orkin

(57) ABSTRACT

A method for joining and holding closed a wound in bodily tissue, fastening junctions of wounds, tying off wounds, joining a foreign element to tissue, and altering the position of tissue using a barbed suture including sharp pointed ends. Each end of the suture includes barbs on that permit movement in an opposing direction to the barbs on the other end of the suture. This two-way barbed suture is used by the method of the present invention in applications including abdominal surgeries such as a Nissen fundoplication, laparoscopic uses such as stabilizing a bowel structure and performing a closure of a cystostomy, liver to bowel anastomosis, closure of an orifice of a Zenker's Diverticulum, endoscopic uses such as closure of ulcerative lesions or and post-procedural tissue defects, bladder wound closure, valve replacement surgery, device attachment, cosmetic surgery, and blood vessel wound closure.

2 Claims, 37 Drawing Sheets

(56) References Cited

U.S. PATENT DOCUMENTS

| | | |
|---|---|---|
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Eaton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling et al. |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,990,144 A | 11/1976 | Schwartz |
| 4,006,747 A | 2/1977 | Kronenthal |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey et al. |
| 4,434,796 A | 3/1984 | Karapetian et al. |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,719,917 A | 1/1988 | Barrows et al. |
| 4,741,330 A | 5/1988 | Hayhurst |
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 S | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schutz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |

(56) References Cited

U.S. PATENT DOCUMENTS

| | | |
|---|---|---|
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green et al. |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A * | 1/1996 | Le et al. .................. 606/232 |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A * | 6/1996 | Pietrzak et al. .............. 606/232 |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A * | 1/1997 | Northrup, III ............... 606/232 |
| 5,601,557 A | 2/1997 | Hayhurst et al. |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |

(56) References Cited

U.S. PATENT DOCUMENTS

| | | |
|---|---|---|
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 5,320,629 B1 | 5/2000 | Noda et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A * | 12/2000 | Bonutti et al. ................ 606/232 |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 * | 9/2003 | Schaller et al. ................ 606/157 |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Lendlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,063,716 B2 | 6/2006 | Cunningham |

(56) References Cited

U.S. PATENT DOCUMENTS

| | | |
|---|---|---|
| 7,070,610 B2 | 7/2006 | Im et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,150,757 B2 | 12/2006 | Fallin et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 8,118,834 B1 | 2/2012 | Goraltchouk et al. |
| 8,216,273 B1 | 7/2012 | Goraltchouk et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173822 A1 | 11/2002 | Justin et al. |
| 2002/0179718 A1 | 12/2002 | Murokh et al. |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency et al. |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0038472 A1 | 2/2005 | Furst |
| 2005/0055051 A1 | 3/2005 | Grafton |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0203576 A1 | 9/2005 | Sulamandize et al. |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0283246 A1 | 12/2005 | Cauthen, III et al. |
| 2006/0030884 A1 | 2/2006 | Young et al. |
| 2006/0036266 A1 | 2/2006 | Sulamanidze et al. |
| 2006/0058574 A1 | 3/2006 | Priewe et al. |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0193769 A1 | 8/2006 | Nelson et al. |
| 2006/0200062 A1 | 9/2006 | Saadat |
| 2006/0235445 A1 | 10/2006 | Birk et al. |
| 2006/0235447 A1 | 10/2006 | Walshe |
| 2006/0257629 A1 | 11/2006 | Lendlein et al. |
| 2006/0282099 A1 | 12/2006 | Stokes et al. |
| 2007/0021779 A1 | 1/2007 | Garvin et al. |
| 2007/0065663 A1 | 3/2007 | Trull et al. |
| 2007/0088135 A1 | 4/2007 | Lendlein et al. |
| 2007/0134292 A1 | 6/2007 | Suokas et al. |

(56) References Cited

U.S. PATENT DOCUMENTS

| | | |
|---|---|---|
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0225642 A1 | 9/2007 | Houser et al. |
| 2007/0282247 A1 | 12/2007 | Desai et al. |
| 2008/0009902 A1 | 1/2008 | Hunter et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0195147 A1 | 8/2008 | Stopek |
| 2008/0234731 A1 | 9/2008 | Leung et al. |
| 2008/0255611 A1 | 10/2008 | Hunter |
| 2008/0262542 A1 | 10/2008 | Sulamanidze et al. |
| 2009/0012560 A1 | 1/2009 | Hunter et al. |
| 2009/0018577 A1 | 1/2009 | Leung et al. |
| 2009/0107965 A1 | 4/2009 | D'Agostino |
| 2009/0112259 A1 | 4/2009 | D'Agostino |
| 2009/0143819 A1 | 6/2009 | D'Agostino |
| 2009/0226500 A1 | 9/2009 | Avelar et al. |
| 2009/0299408 A1 | 12/2009 | Schuldt-Hempe et al. |
| 2010/0057123 A1 | 3/2010 | D'Agostino et al. |
| 2010/0087855 A1 | 4/2010 | Leung et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2011/0009902 A1 | 1/2011 | Leung et al. |
| 2011/0046669 A1 | 2/2011 | Goraltchouk et al. |
| 2011/0166597 A1 | 7/2011 | Herrmann et al. |

FOREIGN PATENT DOCUMENTS

| | | |
|---|---|---|
| CN | 2640420 | 9/2004 |
| DE | 1810800 | 6/1970 |
| DE | 03227984 | 2/1984 |
| DE | 4302895 | 8/1994 |
| DE | 19618891 | 4/1997 |
| DE | 198 33 703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0428253 B1 | 5/1991 |
| EP | 0513713 | 5/1992 |
| EP | 0632999 | 1/1995 |
| EP | 0513736 | 2/1995 |
| EP | 0464479 | 3/1995 |
| EP | 0464480 | 3/1995 |
| EP | 0576337 | 3/1997 |
| EP | 0576337 B1 | 5/1997 |
| EP | 0574707 | 8/1997 |
| EP | 0612504 | 11/1997 |
| EP | 0 826 337 | 3/1998 |
| EP | 0558993 | 4/1998 |
| EP | 0 839 499 | 5/1998 |
| EP | 0913123 | 5/1999 |
| EP | 0916310 | 5/1999 |
| EP | 0664198 | 6/1999 |
| EP | 0960600 | 12/1999 |
| EP | 1075843 | 2/2001 |
| EP | 0705567 | 3/2002 |
| EP | 0673624 | 8/2002 |
| EP | 0755656 | 12/2003 |
| EP | 1525851 | 4/2005 |
| EP | 1532942 | 5/2005 |
| EP | 0991359 | 11/2007 |
| EP | 2338421 | 11/2012 |
| FR | 2619129 | 2/1989 |
| FR | 2693108 | 6/1992 |
| FR | 9208059 | 3/1997 |
| GB | 0267007 | 3/1927 |
| GB | 1091282 | 11/1967 |
| GB | 1 428 560 | 3/1976 |
| GB | 1506362 | 4/1978 |
| GB | 1508627 | 4/1978 |
| JP | 51-130091 | 11/1976 |
| JP | 1506362 | 4/1978 |
| JP | 54-116419 | 9/1979 |
| JP | 63-500702 | 3/1988 |
| JP | 63-288146 | 11/1988 |
| JP | 001113091 | 5/1989 |
| JP | 3-165751 | 7/1991 |
| JP | 4-096758 | 3/1992 |
| JP | 4-226642 | 8/1992 |
| JP | 4-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2005-500119 | 1/2005 |
| JP | 2006-517112 | 7/2006 |
| JP | 2009-118967 | 6/2009 |
| KR | 10-2005-0072908 A | 7/2005 |
| KR | 6013299 | 2/2006 |
| KR | 2006-59142 | 6/2006 |
| NZ | 501224 | 3/2002 |
| NZ | 531262 | 12/2005 |
| RU | 1823791 | 6/1993 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 03/001979 | 1/2003 |
| WO | WO 03/003925 | 1/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 A1 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |

(56) References Cited

FOREIGN PATENT DOCUMENTS

| | | |
|---|---|---|
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/112787 | 12/2005 |
| WO | WO 2006/079469 | 8/2006 |
| WO | WO 2007/005291 | 1/2007 |
| WO | WO 2007/005296 | 1/2007 |
| WO | WO 2007/053812 | 5/2007 |
| WO | WO 2007/089864 | 8/2007 |
| WO | WO 2008/128113 | 10/2008 |
| WO | WO 2008/150773 | 12/2008 |
| WO | WO 2009/042841 | 4/2009 |
| WO | WO 2009/097556 | 8/2009 |
| WO | WO 2009/151876 | 12/2009 |

OTHER PUBLICATIONS

"Drilled End Surgical Needles", B.G. Sulzle, Inc., Syracuse, New York, Jul. 2002.

Sulamanidze, M.A., et al.; "Facial Lifting with "Aptos" Threads", Jul. 18, 2001, www.fonendo.com, pp. 1-6.

Dattilo, Jr., Philip P., et al.; "Medical Textiles: Application of an Absorbable Barbed Bi-directional Surgical Suture", Journal of Textile and Apparel, Technology and Management, vol. 2, Issue 2, Spring 2002; RTP, North Carolina.

"Up Lifting (Aptos Threads)", http://www.ccpr.com.br/upl-l.htm, Aug. 19, 2002, pp. 1-2.

Han, Hougtao, et al.; "Mating and Piercing Micromechanical Structures for Surface Bonding Applications" Micro Electro Mechanical Systems, (MEMS-91), Nara, Japan, Jan. 31-Feb. 2, 1991, CH2957-9/9, pp. 253-258, 1991.

Buncke, Jr., H. J., et al.; "The Suture Repair of One-Millimeter Vessels" Micro-Vascular Surgery; Report of First Conference, Oct. 6-7, 1966. pp. 24-35 (esp. p. 34), 1966; USA.

Sulamanidze, M.A., et al.; "Removal of Facial Soft Tissue Ptosis With Special Threads" Dermatol Surg 2002, 28, pp. 367-371; Blackwell Publishing, Inc.

Declaration of Dr. Gregory L. Ruff, Dated Aug. 19, 2005, 8 pages, with Exhibits A-E.

Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.

Bunnell, S. 'Gig pull-out suture for tendons' J Bone Joint Surg. Am (1954) vol. 36A, No. 4 pp. 850-851.

Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.

Dattilo, Jr., P. et al 'Tissue holding performance of knotless absorbable sutures' Society for Biomaterials 29th Annual Meeting Transactions (2003) p. 101.

Encyclopedia of Polymer Science and Engineering, edited by H.F. Mark, et al. Wiley-Interscience, New York, 1989.

Gross, R.A. et al 'Biodegradable Polymers for the Environment' Science 297(5582) 803 (2002).

Ingle, N. P. et al 'Mechanical Performance and Finite Element Analysis of Bi-directional Barbed Sutures' Master of Science in Textile Technology & Management at North Carolina State University Aug. 2003, 126 pages.

Jennings et al 'A New Technique in primary tendon repair' Surg. Gynecol. Obstet. (1952) vol. 95, No. 5 pp. 597-600.

Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.

Lendlein, A. et al 'Biodegradable, Elastic Shape-Memory Polymers for Potential Biomedical Applications' (2002) Science vol. 296 pp. 1673-1676.

Lendlein, A. et al 'Shape-Memory Polymers' Agnew Chem. Int. Ed. (2002) vol. 41 pp. 2034-2057.

Leung, J. et al 'Barbed, Bi-directional Medical Sutures: Biomechanical Properties and Wound Closure Efficacy Study' 2002 Society for Biomaterials 28th Annual Meeting Transactions 1 page.

Leung, J. et al 'Barbed, Bi-directional Surgical Sutures' International Conference & Exhibition on Healthcare & Medical Textiles, Jul. 8-9, 2003 pp. 1-8.

Leung, J. et al 'Barbed, Bi-directional Surgical Sutures: In Vivo Strength and Histopathology Evaluations' 2003 Society for Biomaterials 29th Annual Meeting Transactions pp. 100.

Li, Y.Y. et al 'Polymer Replicas of Photonic Porous Silicon for Sensing and Drug Delivery Applications' (2003) Science vol. 299 pp. 2045-2047.

Malina, M. et al 'Endovascular AAA Exclusion: Will Stents with Hooks and Barbs Prevent Stent-Graft Migration' Journal Endovascular Surgery (1998) vol. 5 pp. 310-317.

Manual for the Rubber Industry, 2nd ed. Bayer AG, Akron, Ohio, 1993.

Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.

Mark, J.E. ed. Physical Properties of Polymers Handbook. American Institute of Physics Press, Woodbury, N.Y., 1996.

Martin, D.P. et al 'Medical applications of poly-4-hydroxybutyrate: a strong flexible absorbable biomaterial' Biochemical Engineering Journal vol. 16 (2003) pp. 97-105.

Mason, M.L. 'Primary and Secondary Tendon Suture. A discussion of the significance of technique in tendon surgery' (1940) Surg Gynecol Obstet 70.

McKee, GK 'Metal anastomosis tubes in tendon suture' The Lancet (1945) pp. 659-660.

Middleton and Tipton 'Synthetic Biodegradable Polymers as Medical Devices' (1998) Medical Plastics and Biomaterials Magazine, 9 pages.

Potenza, A. 'Tendon Healing Within the Flexor Digital Sheath in the Dog: An Experimental Study' Journal of Bone & Joint Surgery (1962) vol. 44A No. 1 pp. 49-64.

Pulvertaft 'Suture Materials and Tendon Junctures' American Journal of Surgery (1965) vol. 109 pp. 346-352.

Rofin-Baasel 'Laser Marking on Plastic Materials' (2001) RB50.0, Rofin-Baasel Inc. 2 pages.

Schmid A. et al 'The outspreading anchor cord. A material for arthroscopic suturing of a fresh anterior cruciate ligament rupture' Surgical Clinic of the University of Gottingen' (1987) pp. 417-426.

Semenov, G.M. et al 'Surgical Suture' (2001) Piter, Saint Petersburg, pp. 12-13 and 92-98.

Serafetinides, AA 'Short pulse laser beam interactions with polymers biocompatible materials and tissue' Proce SPIE vol. 3052 (1996) pp. 111-123.

Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.

Sulamanidze, M.A. et al 'Facial lifting with Aptos threads' International Journal of Cosmetic Surgery and Aesthetic Dermatology' (2001) No. 4 pp. 1-8.

Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.

Sulamanidze, M.A. et al 'Morphological foundations of facelift using APTOS filaments' Bolshaya Serpukhovskaya ul 27, 113811 Moscow, Russia (2002) pp. 19-26.

Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.

Verdan, C. 'Primary Repair of Flexor Tendons' Journal of Bone and Joint Surgery (1960) vol. 42, No. 4 pp. 647-657.

(56) References Cited

OTHER PUBLICATIONS

Zoltan, J. 'Cicatrix Optimia: Techniques for Ideal Wound Healing' English language edition University Park Press Baltimore (1977) Chapter 3 pp. 54-55.
Communication from EPO re: 10000486 dated Apr. 4, 2011.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pages.
International Search Report for PCT/US2003/030424 dated Nov. 1, 2004.
International Search Report for PCT/US2003/030664 dated May 25, 2004.
International Search Report for PCT/2003/030666 dated Dec. 15, 2004.
International Search Report for PCT/US2003/25088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/0064921 dated Nov. 19, 2008, 3 pages.
International Search Report for PCT/US2008/075849 dated Mar. 18, 2009, 4 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/059238 dated May 21, 2012.
International Search Report for PCT/US2011/060069 dated May 18, 2012.
International Search Report for PCT/US2012/030441 dated Sep. 27, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Singapore Search Report for Singapore Patent Application No. 201103117-6 dated Mar. 8, 2013.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 05750101 dated Apr. 7, 2010.
Supplementary European Search Report re: 07017663 dated Nov. 7, 2007.
Written Opinion of the International Searching Authority re: PCT/US2010/056898 dated Jul. 29, 2011.

* cited by examiner

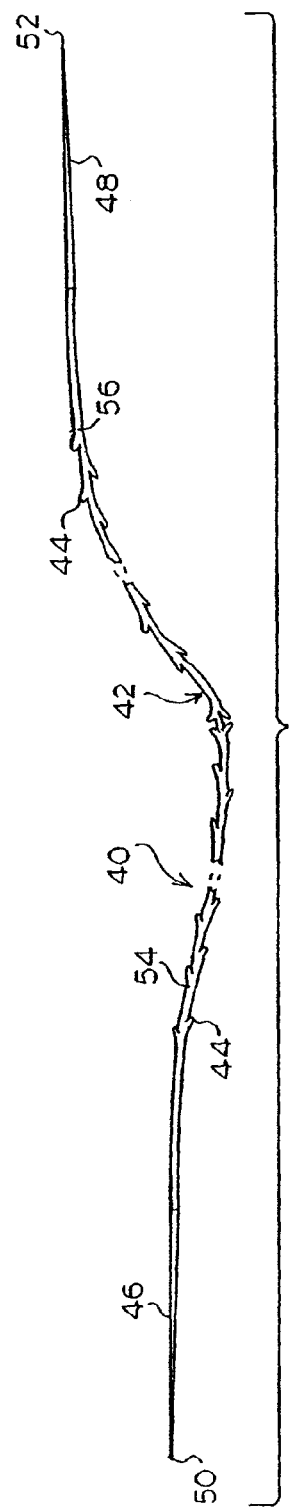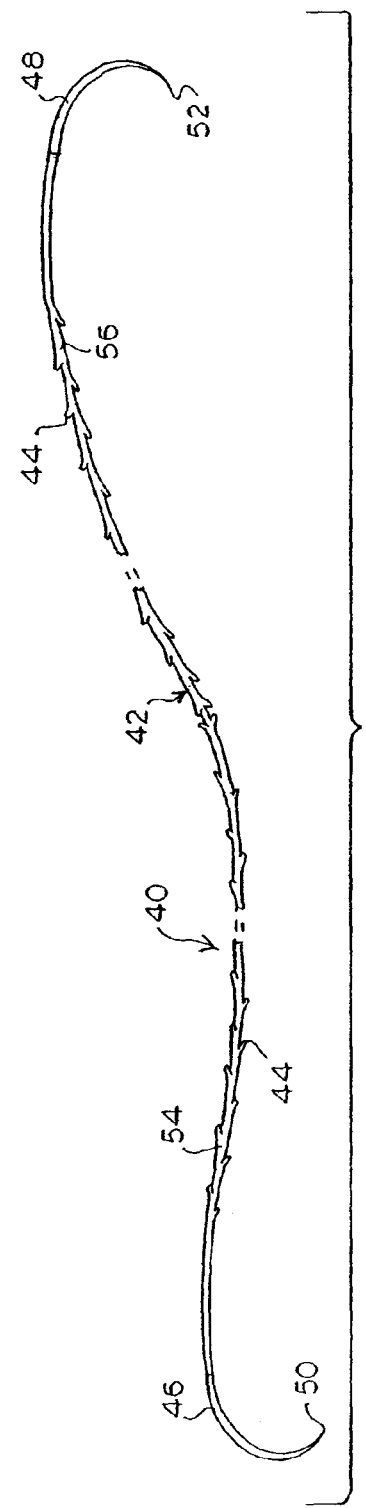
FIG. 1
FIG. 2

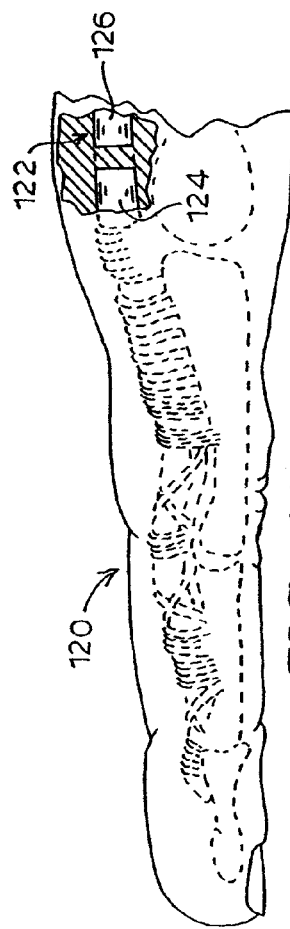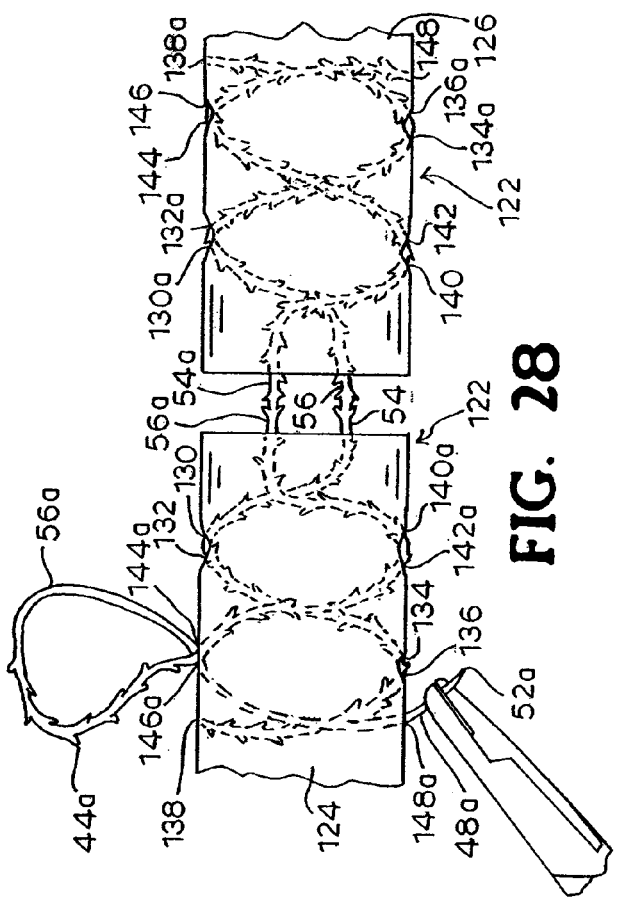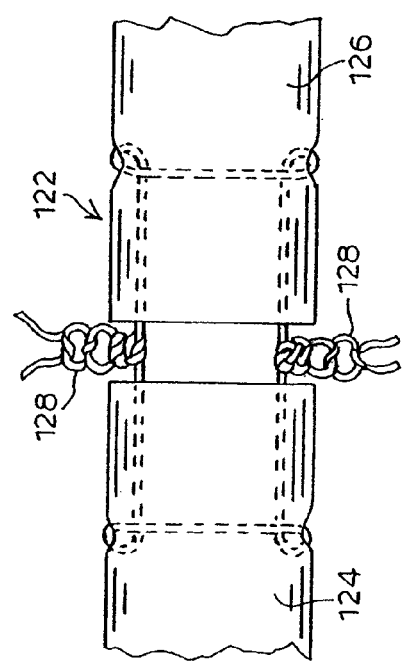
FIG. 23
FIG. 28
FIG. 24 PRIOR ART

SUTURE METHOD

RELATED APPLICATIONS

This application is a divisional application of U.S. patent application Ser. No. 10/065,256, filed Sep. 30, 2002, now U.S. Pat. No. 7,056,331, which is a continuation-in-part of U.S. patent application Ser. No. 09/896,455, filed Jun. 29, 2001, now U.S. Pat. No. 6,599,310, the contents of both of which are hereby incorporated by reference.

BACKGROUND

This invention relates generally to a method for joining bodily tissue in surgical applications and wound repair, and more particularly to a surgical suturing method for joining bodily tissue using a suture having a plurality of barbs which permit the suture to be pulled through the tissue in one direction but resisting movement of the suture relative to the tissue in the opposite direction.

Surgical or accidental wounds are typically closed with a length of filament introduced into the tissue by a sharp metal needle attached to one end of the filament. This device is known as a "suture". Sutures are used to make "stitches" to close the wound for holding tissues together for healing and regrowth. Sutures are used in surgical procedures for wound closure, to close the skin in plastic surgery, to secure damaged or severed tendons, muscles or other internal tissues, and in microsurgery on nerves and blood vessels. Generally, the suture needle is caused to penetrate and pass through the tissue pulling the suture through the tissue. The opposing faces of the tissue are then moved together, the needle is removed, and the ends of the suture are tied in a knot. The suture forms a loop as the knot is tied. The knotting procedure allows the tension on the filament to be adjusted to accommodate the particular tissue being sutured and control of approximation, occlusion, attachment or other conditions of the tissue. The ability to control tension is extremely important regardless of the type of surgical procedure being performed.

Suturing is a time-consuming part of most surgical procedures, particularly in microsurgery and endoscopic surgery where there is insufficient space to properly manipulate the suture. Loop sutures can leave scars where they penetrate skin. For adequate closure of some wounds, the suture material must be of a high tensile strength and thus a large diameter thereby increasing scarring. The loop suture also constricts blood flow to the tissue it surrounds, promoting necrosis of the wound margins which compromises healing and increases infection risks. Further, the tissue is distorted as it is secured by the suture loop due to excess tension on the knots. Localized tensions from the knots are the culprit for scar formation. The bulk of the knots are also an impediment to wound healing in internal applications.

Alternatives to conventional sutures for wound closure are known, including fasteners such as staples, clips, tacks, clamps and the like. The fasteners are usually positioned transversely across a wound for joining or approximating each side of adjacent tissue layers laterally. Fasteners have relatively high strength and save time, but are not as accurate as sutures and are bulky and may be painful to remove. Fasteners are also generally unsuitable for deeper layers of tissue. Moreover, fasteners do not provide the advantage of adjustable tension obtained by the knotting of a length of suture material.

Surface adhesive tapes and glues are often used on skin to hold small wounds closed to permit healing. However, these products have relatively low tensile strength and are not useful in many situations.

Other techniques proposed include electrical coagulation and lasers. However, no acceptable alternative has been found which offers the advantages of suturing and tying in most surgical procedures.

One possible alternative is a barbed suture. A barbed suture includes an elongated body having one or more spaced barbs projecting from the surface of the body along the length of the body. The barbs are configured to allow passage of the suture in one direction through tissue but resist movement of the suture relative to the tissue in the opposite direction. In wound closure, a barbed suture is passed through tissue at each of the opposed sides of a wound. The wound is closed by pushing the sides of the wound together with the barbs maintaining the sutures in place and resisting movement of the tissue away from this position. The advantage of using barbed sutures is the ability to put tension in the tissue with less slippage of the suture in the wound. The barbed suture spreads out the holding forces evenly thereby significantly reducing tissue distortion. Since knots do not have to be tied, there is a time savings and the elimination of suture knots improves cosmetic effects and promotes wound healing. Barbed sutures also allow better apposition of tissue since the incised or insulted tissues are brought together and secured with almost no movement immediately. Unlike the conventional suturing method wherein tension is applied by pulling on the end of the suture after placement, barbed sutures permit tissue to be approximated and held snug during suturing. This is especially advantageous in closing long incisions. The result is better healing when the tissue levels are harmoniously matched as the cosmetic effect is more pronounced at skin level. Moreover, if there is an accidental breakage of the barbed suture, the wound is minimally disturbed. With conventional sutures, dehiscence would occur.

Despite the advantages offered by barbed sutures, the tensile strength of a barbed suture is less than a loop suture of equivalent size. This is due to the reduced tensile strength resulting from imparting the barb structure onto the body of the suture, which reduces its effective diameter. This limitation is not significant since larger barbed sutures with greater tensile strength can be utilized. However, the conventional methods for introducing barbed sutures into tissue still do not exhibit the same biomechanical performance of looped sutures.

For the foregoing reasons there is a need for a suturing method for joining tissue in surgical applications and wound repair which is efficient and expedites the surgical procedure. Ideally, the new method allows a surgeon to suture in an efficient manner to quickly approximate tissue with appropriate tension. The new method should preserve blood flow, improve wound healing strength, prevent distortion of the tissue and minimize scarring. The method should also incorporate the self-retaining benefits of the barbed suture with the holding power of conventional suturing methods. A particularly useful method would be utilized in surgical applications where space is limited such as microsurgery, endoscopic surgery, or arthroscopic surgery.

SUMMARY

The present invention provides a way to close wounds, fasten junctions of tissue, tie off wounds, join a foreign element to tissue, mount a device to tissue, alter the position of tissue where there is only a single portion of tissue without a wound or junction, and perform other procedures. The methods of the present invention are performed with a two-way barbed suture. Specifically, the two-way barbed suture includes an elongated body, first and second sharp pointed distal ends for penetrating the tissue, and a plurality of barbs extending from the periphery of the body. The barbs on a first portion of the body between the first end of the suture and a first axial location on the body permit movement of the suture through the tissue in a direction of movement of the first end, and prevent movement of the suture relative to the tissue in a direction opposite the direction of movement of the first end. The barbs on a second portion of the body between the second end of the suture and a second axial location on the body, which is less than the distance from the second end to the first axial location, permit movement of the suture through the tissue in a direction of movement of the second end, and prevent movement of the suture relative to the tissue in a direction opposite the direction of movement of the second end.

In some embodiments of the present invention an insertion device is used to insert the barbed suture. Such an insertion device is tubular and has leading and trailing ends with openings therein. The suture is initially disposed in the insertion device. The first end of the suture is proximate to the leading end of the insertion device. Where no insertion device is used, the sharp pointed ends of the suture are used to insert the suture in tissue; while these ends may be embodied, or be referred to, as needles herein, it should be understood that the suture may terminate in any type of sharp pointed end.

Some embodiments provide a method for joining and holding portions of a stomach to each other in the performance of a Nissen fundoplication procedure. The Nissen fundoplication procedure requires grasping the fundus of the stomach at a proximal location and pulling the fundus around the esophagus, wrapping the fundus around the esophagus one time and attaching the proximal stomach to an apposing portion of the stomach. One method that uses the sharp pointed ends of the barbed suture to penetrate tissue comprises the steps of inserting the first pointed end of the suture into tissue of the proximal stomach and pushing the first end of the suture through the stomach tissue until the first end of the suture extends out of the tissue at an exit point on the exterior of the stomach. The first end of the suture is pulled to draw the first portion of the suture through the tissue until the second axial location is proximate to the point of insertion of the first end of the suture. A length of the first portion of the suture is left in the tissue between the point of insertion and exit point of the first end. The proximal stomach is gripped and the fundus is wrapped around the esophagus until the proximal stomach contacts an apposing portion of stomach. The second pointed end of the suture is inserted into tissue of the apposing stomach, and the second end of the suture is pushed through the stomach tissue until the second end of the suture extends out of the tissue at an exit point on the exterior of the stomach. The second end of the suture is pulled to draw the second portion through the tissue until the second axial location is proximate to the point of insertion of the second end of the suture and a length of the second portion of the suture is left in the tissue between the point of insertion and exit point of the second end.

In another embodiment of a Nissen fundoplication method, an insertion device is used. Again, the fundus is wrapped around the esophagus to form a junction with the apposing portions of stomach. Then the first pointed end of the suture and leading end of the insertion device are inserted into stomach tissue at a point laterally spaced from the junction and on a first side of the junction. The first end of the suture and leading end of the insertion device are pushed through the first side of stomach tissue and penetrate the stomach tissue on a second side of the junction until the portion of the suture between the first and second axial locations is proximate to the junction. The insertion device is removed by gripping and pulling the trailing end, leaving the suture in place.

Another embodiment for performing a Nissen fundoplication is provided using both sharp pointed ends of the suture, comprising the step of inserting the first pointed end of the suture into the tissue at a first side of the junction formed by the wrapping of the fundus around the esophagus. The first end of the suture is pushed through the tissue until the first end of the suture extends out of the tissue at an exit point in the face of the junction below the surface of the tissue at the first side of the junction. The first end is pulled out of the tissue, drawing the first portion of the suture through the tissue until the second axial location is at the point of insertion of the first end of the suture. A length of the first portion of the suture is left in the tissue between the point of insertion in the first side of the junction and the exit point in the face of the junction at the first side of the junction. The first end of the suture is then inserted into the face of the tissue below the surface of the tissue at a second side of the junction, and is pushed until the first end exits on the second side of the junction longitudinally spaced in a first direction from the insertion point in the first side of the junction. The first end of the suture is pulled out of the tissue and the first portion is drawn to bring the two sides of the junction together to a closed position along the first portion of the suture in the tissue. A length of the first portion of the suture is left in the tissue between the point of insertion in the first side of the junction and the exit point in the second side of the junction. The process is repeated similarly for the second end and second portion of the suture.

Another method for joining and holding portions of a stomach to each other in the performance of a Nissen fundoplication is provided, using the sharp pointed ends of the suture, which may be needles. The method comprises the steps of inserting the first pointed end of the suture into the stomach tissue below the surface of the stomach tissue at a first face of the junction at an initial point. The first end of the suture is pushed through the stomach tissue along a curvilinear path until the first end of the suture extends from the stomach tissue at an exit point in the first face of the junction. This exit point is longitudinally spaced in a first direction from the insertion point in the first face of the junction. The first pointed end of the suture is gripped and pulled until it is out of the stomach tissue, drawing the first portion of the suture through the stomach tissue until the second axial location is at the point of insertion of the first end of the suture in the first face of the junction, leaving a length of the first portion of the suture in the stomach tissue of the junction. The first pointed end is inserted at a point below the surface of the stomach tissue in a second face of the junction, and pushed through the stomach tissue along a curvilinear path until the first end of the suture extends from the stomach tissue at an exit point in the second face of the junction below the surface of the stomach tissue. Again, the exit point is longitudinally spaced in the first direction from the insertion point in the second face of the junction. Then the first end of the suture is inserted at a point in the first face of the junction below the surface of the stomach tissue, and the above steps may be repeated for advancing along the junction in the first direction as necessary to one end of the junction. These steps are similarly repeated for the second end and second portion of the suture in a second direction. The initial point may be longitudinally spaced from the ends of the junction or adjacent to an end, and the first and second directions may be the opposite or same directions.

One embodiment provides a method for laparoscopically inserting a barbed suture with a laparoscopic insertion device, similar to the insertion device described above but included in a laparoscopic tool. The first pointed end of the suture and the leading end of the laparoscopic insertion device are inserted through an entry point in the skin, and then through the fat, fascia, muscle, and peritoneum into the abdominal cavity. The first end of the suture and leading end of the insertion device are pushed into the tissue in the abdominal cavity, and the insertion device is pulled at the trailing end to remove the insertion device. Additional embodiments include stabilizing a bowel structure, where the bowel structure is positioned and then stabilized by leaving the inserted suture in place in the bowel tissue and the abdominal wall, and for a closure for a cytostomy, in which the first and second ends and portions of the suture are inserted in urinary bladder muscularis.

Another embodiment involves a method for performing an anastomosis of the liver bile duct to a bowel structure, the bile duct having one end connected to the liver and a free end after having been severed, and the bowel structure having an opening in its wall made to receive the annular free end of the bile duct. One embodiment is performed with an insertion device as described above, with steps comprising placing the free end of the bile duct in contact with the opening in the bowel structure, and forming a junction at the annular contact area between the bile duct tissue and the bowel structure tissue. The first pointed end of the suture and the leading end of the insertion device are inserted into the tissue on one side of the junction. The first end of the suture and leading end of the insertion device are pushed through the tissue on one side of the junction, through the junction, and penetrate the tissue on the other side of the junction. The insertion device is gripped and pulled at the trailing end to remove the insertion device, leaving the suture in place in both the bile duct tissue and the bowel structure tissue. The previous steps are repeated as necessary to provide an anastomotic seal at the junction.

In another embodiment, a liver bile duct-to-bowel structure anastomosis is performed with needles. Here, the first pointed end of the suture is inserted into a first tissue at a point spaced from the junction of the duct and bowel structure. The first end of the suture is pushed through the first tissue until the first end of the suture extends out of the first tissue at an exit point and penetrates a second tissue at a face of the junction. The first end of the suture is pushed until the first end of the suture extends out of the second tissue at an exit point spaced from the junction and spaced in a first direction along the circumference of the junction from the point of insertion of the first end of the suture in the first tissue. The first end of the suture is gripped and pulled out of a second tissue to draw the first portion of the suture through the first tissue and the second tissue while bringing the first tissue and the second tissue together to a closed position along the first portion of the suture. This pulling continues until the second axial location is at the point of insertion of the first end of the suture at the one side of the first tissue, leaving a length of the first portion of the suture in the first tissue and the second tissue between the point of insertion and the exit point. Then the first end of the suture is inserted into the second tissue at the exit point of the first end. The first end of the suture is pushed through the second tissue until the first end of the suture extends out of the second tissue at an exit point in the face of the junction and penetrates the first tissue. This pushing continues until the first end of the suture extends out of the first tissue at an exit point spaced from the junction and spaced along the circumference of the junction in the first direction from the immediately preceding point of insertion of the first end of the suture in the first tissue. Then first end of the suture is pulled out of the tissue to draw the first portion of the suture through the second tissue while bringing the first tissue and the second tissue together to a closed position along the first portion of the suture, and leaving a length of the first portion of the suture in the periphery between the point of insertion and the exit point. The above steps for the first end and first portion may be repeated to achieve an anastomotic seal. In addition, the steps described above are repeated similarly for the second end and second portion of the suture in a second direction.

In another embodiment, a method for tying off an appendiceal stump resulting from the performance of an appendectomy is provided, using needles. The appendix extends from the cecum of the large intestine and has a base with a circumference at the juncture of the appendix and the cecum. The first pointed end of the suture is inserted into tissue of the cecum proximate to the appendix base. The first end of the suture is pushed around the circumference of the base in one direction for at least one half of the circumference of the base until extending through an exit point in the tissue. The second pointed end of the suture is then inserted into tissue of the cecum proximate to the entry point of the first end, and the second end of the suture is pushed along the circumference of the base in the other direction for at least one half of the circumference of the base until extending through an exit point in the tissue. The appendix is excised, leaving the appendiceal stump. Then the ends of the suture are gripped and pulled, causing the suture to tighten around the appendiceal stump, and may invert the stump into the cecum.

Another embodiment provides a method for joining and holding closed the muscle layers that define the orifice of a Zenker's Diverticulum using an endoscopic insertion device, similar to the insertion device described above but included in an endoscopic tool. The Zenker's Diverticulum includes a sac extending from a proximal location of the esophagus near the pharynx, the sac having walls including a muscle layer common to the proximal esophagus. The Zenker's Diverticulum may first be manually inverted into the esophagus, or left outside the esophagus. The first pointed end of the suture and the leading end of the endoscopic insertion device are inserted through an entry point in the esophageal muscle between the pharynx and the orifice, and spaced from the orifice. The first end of the suture and leading end of the insertion device are pushed through the muscle until the first end of the suture and the leading end of the insertion device extend out of the muscle at the orifice of the sac. Then the first pointed end of the suture and the leading end of the endoscopic insertion device are inserted through an opposing side of the orifice, and are pushed through the muscle until the second axial location is proximate to a central to the point of the orifice. The insertion device is gripped and pulled at the trailing end to remove the insertion device, leaving the suture in place. Optionally, the above steps may be repeated with additional sutures. The muscle on the two sides of the orifice is advanced together as necessary to close the orifice.

A method is provided for joining and holding closed ulcerative lesions or post-procedural tissue defects on an interior surface of a viscus, using an endoscopic insertion device as described above. The method comprises the step of inserting the first pointed end of the suture and the leading end of the endoscopic insertion device through an entry point in the tissue spaced from and on one side of the lesion. Then the first end of the suture and leading end of the insertion device are pushed through the tissue until the first end of the suture and the leading end of the insertion device extend out of the tissue at the lesion. The first pointed end of the suture and the leading end of the endoscopic insertion device are then inserted through an opposing side of the lesion, and are pushed until the second axial location is proximate to a central to the point of the lesion. The insertion device is gripped and pulled at the trailing end to remove the insertion device, leaving the suture in place. Again, optionally the above steps may be repeated. The tissue on the two sides of the lesion is advanced together to close the lesion.

In another embodiment, a method is provided for joining and holding closed a wound in urinary bladder muscularis tissue, using needles. The first pointed end of the suture is inserted into the tissue below the surface of the tissue at a first face of the wound at an initial point, which may for example be adjacent to one end or longitudinally spaced from both ends of the wound. The first end of the suture is pushed through the tissue along a curvilinear path until the first end of the suture extends from the tissue at a subcutaneous exit point in the first face of the wound and longitudinally spaced in a first direction from the insertion point in the first face of the wound. The first pointed end of the suture is gripped and pulled out of the tissue, drawing the first portion of the suture through the tissue until the second axial location is at the point of insertion of the first end in the first face of the wound and leaving a length of the first portion of the suture in the tissue of the wound. Then the first pointed end of the suture is inserted at a point below the surface of the tissue in a second face of the wound. The first end is pushed through the tissue along a curvilinear path until the first end extends from the tissue at an exit point in the second face of the wound below the surface of the tissue and longitudinally spaced in the first direction from the insertion point in the second face of the wound. The first end of the suture is inserted at a point in the first face of the wound below the surface of the tissue. The above steps are repeated starting with the insertion of the first end of the suture in the first face of the wound to advance longitudinally along the wound in the first direction until reaching the end of the wound. Further, all of the above steps are repeated for the second end and second portion of the suture, in a second direction, starting with inserting the second end in the second face of the wound below the surface of the tissue and adjacent the initial point of insertion of the first end in the first face of the wound.

Another method is provided for joining and holding closed a wound in urinary bladder muscularis tissue, also using needles. The first pointed end of the suture is inserted into the muscularis tissue below the surface of the tissue of a first face of the wound at an initial point adjacent an end of the wound. The first end of the tissue is pushed through the tissue along a curvilinear path until the first end of the suture extends from the tissue at an exit point in the first face of the wound below the surface of the tissue and longitudinally spaced from the end of the wound in a direction toward the other end of the wound. The first pointed of the suture is gripped and pulled out of the tissue, drawing the first portion of the suture through the tissue until the second axial location is at the point of insertion of the first end in the first face of the wound and leaving a length of the first portion of the suture in the tissue of the wound. The first end of the suture is then inserted into the second face of the wound below the surface of the tissue. The first end of the suture is pushed through the tissue along a curvilinear path until the first end extends from the tissue at an exit point in the second face of the wound below the surface of the tissue and longitudinally spaced from the insertion point in the second face of the wound toward the other end of the wound. The first end of the suture is inserted into the first face of the wound below the surface of the tissue, and the above steps are repeated starting with pushing the first end through the tissue until extending from an exit point in the first face of the wound, advancing longitudinally along the wound until reaching the other end of the wound. The steps are repeated similarly for the second end and second portion of the suture, starting with inserting the second end of the suture into the tissue of the second face of the wound below the surface adjacent the point of insertion of the first end.

An embodiment of a method is provided for joining a foreign element and bodily tissue, either of which may be referred to as first matter or second matter, using needles. The foreign element has a periphery and the bodily tissue has a fibrous tissue ring with a face of the fibrous tissue ring defining an opening and apposing a face of the periphery, and holding closed a junction between the element and the tissue. The first pointed end of the suture is inserted into the periphery of the foreign element at a point radially spaced from the face of the fibrous tissue ring. The first end of the suture is pushed through the periphery until the first end of the suture extends out of the periphery at an exit point and penetrates the tissue of a face of the fibrous tissue ring until the first end of the suture extends out of the tissue at an exit point radially spaced from the junction and spaced along the fibrous tissue ring circumference in a first direction from the point of insertion of the first end of the suture on the periphery. The first end of the suture is gripped and pulled, drawing the first portion of the suture through the periphery and the tissue while bringing the periphery and the tissue together to a closed position along the first portion of the suture. This continues until the second axial location is at the point of insertion of the first end of the suture in the periphery and a length of the first portion of the suture is left in the periphery and the tissue between the point of insertion and the exit point. Then the first end of the suture is inserted into the tissue at the exit point of the first end. The first end is pushed through the tissue until the first end extends out of the tissue at an exit point in the face of the fibrous tissue ring and penetrates the periphery until the first end extends out of the periphery at an exit point radially spaced from the junction and spaced along the circumference of the fibrous tissue ring in the first direction from the immediately preceding point of insertion of the first end of the suture in the periphery. The first end of the suture is gripped and pulled out of the periphery, drawing the first portion of the suture through the periphery and tissue while bringing the periphery and the tissue together to a closed position along the first portion of the suture, and leaving a length of the first portion of the suture in the periphery between the point of insertion and the exit point. The above steps are repeated, with each repetition advancing the suture around the circumference of the junction in a first direction Further, the above steps are repeated similarly for a second end and second portion of the suture, in a second direction. In addition, a similar method may be carried out with the suture first being inserted in the tissue rather than in the periphery of the foreign element. The sutures may extend completely around the circumference of the junction, and may overlap one quarter or more of the circumference. Yet another embodiment provides that the suture enter and exit tissue on the face of the junction, and not exit on the surface of the foreign element or the tissue. Examples of applications of these methods include placement of bioprosthetic heart valves, mechanical prosthetic heart valves, and bioprosthetics for cardiac septal defects.

Some embodiments include a method of mounting a device to bodily tissue, using needles. The device includes at least one eyelet for securing the device and through which a suture may pass. The method starts with the step of placing the device in a desired position. Then a suture is threaded through the eyelet. The first pointed end of the suture is inserted into tissue and is pushed through the tissue until extending out an exit point. The first end of the suture is gripped and pulled out of the tissue while drawing the first portion of the suture through the tissue, leaving a portion of the suture between the first and second axial locations out of the tissue and leaving a length of the first portion of the suture in the tissue between the point of insertion and exit point of the first end. These steps are repeated for the second end and portion of the suture in a second direction, resulting in the first and second portions of the suture extending in the tissue in generally opposing directions and causing the suture to resist displacement of the device. Examples of devices that may be mounted according to the present invention include catheters, electrodes of cardiac pacemakers, and tumor monitors. The device may be mounted internally, for example, to an organ, or externally to the epidermis.

Further, methods of performing cosmetic surgery are provided. One embodiment of a procedure using needles begins with inserting the first pointed end at an insertion point on the surface of a person's body. The first end of the suture is pushed through soft tissue until the first end extends out of the soft tissue at an exit point. The first end of the suture is gripped and pulled to draw the first portion of the suture through the soft tissue until the second axial location is proximate to the point of insertion of the first end of the suture, leaving a length of the first portion of the suture in the soft tissue between the point of insertion and exit point of the first end. The second pointed end of the suture is put in place by repeating these steps for the second end and second portion. The soft tissue is manually grouped and advanced along at least one portion of the suture to provide the desired amount of lift.

Specific applications of cosmetic surgeries as described above include, for example, facelifts, browlifts, thigh lifts, and breast lifts. In an embodiment of a facelift, the insertion point is approximately at the temporal hairline, and the first end of the suture is pushed through subepidermal tissue to the exit point of on the scalp. The second end of the suture is pushed through subepidermal tissue, the superficial muscular aponeurotic system, or combinations thereof, to the exit point proximate to the nasolabial fold. Tissue is manually grouped and advanced along the second portion of the suture to provide the desired amount of lift.

In an embodiment of a browlift, the insertion point is on a person's face above the brow line. The first end of the suture is pushed through subepidermal tissue underneath the forehead, scalp, or both and the exit point of the first end of the suture is on the scalp. The second end of the suture is pushed through subepidermal tissue and the exit point of the second end of the suture is proximate to the brow. The tissue is manually grouped and advanced along the second portion of the suture to provide the desired amount of lift. The insertion may be approximately at the frontal hairline or the midpoint between the brow and frontal hairline.

Another embodiment of a browlift is provided for use with needles, and again the insertion point is on a person's face above the brow line. Examples of insertion point locations for browlifts include approximately at the frontal hairline or halfway between the brow and the frontal hairline. The first end of the suture is pushed through subepidermal tissue and the exit point of the first end of the suture is proximate to the brow. The second end of the suture is pushed through subepidermal tissue and the exit point of the second end of the suture is proximate to the brow and spaced from the exit point of the first end of the suture. Then the tissue is manually grouped and advanced along the first and second portions of the suture to provide the desired amount of lift.

An embodiment of a thigh lift is also provided. For a thigh lift, the insertion point is generally at the inguinal crease. The first end of the suture is pushed cranially through subepidermal tissue until the first end of the suture extends out of the tissue. The second end of the suture is pushed caudally through subepidermal tissue until the second end of the suture extends out of the tissue on the thigh, and then tissues are manually grouped and lifted as desired.

Further, a method of performing a cosmetic breast lift is provided. The insertion point is at the upper aspect of the breast curvature, and the first end of the suture is pushed through subcutaneous tissue, dermal tissue, and pectoralis muscle until extending out of the tissue at an exit point on the upper portion of the breast. The second end of the suture is pushed caudally through fibrous and fatty tissues until the second end of the suture extends out of the tissue at an exit point along the anterior aspect or the lower curvature of the breast, and the tissue is manually grouped and lifted as desired.

Embodiments of cosmetic surgery using an insertion device are also provided. In these methods, the first pointed end of the suture and the leading end of the insertion device are inserted at an insertion point. The first end of the suture and the leading end of the insertion device are pushed through tissue beneath the epidermis until reaching an endpoint. Then the insertion device is gripped and pulled at the trailing end to remove the insertion device, leaving the suture in place, and the tissue is manually grouped and advanced along the first portion of the suture to provide the desired amount of lift. This method applies, for example, to a facelift, where the insertion point is in the scalp distal from the temporal hairline. The suture is pushed through the reticular dermis underneath the scalp, and the first end of the suture passes through the temporal hairline, penetrates the facial tissue such as the reticular dermis, the superficial muscular aponeurotic system, or a combination thereof, extending to the nasolobial fold. The method also applies to browlifts, where, for example, the insertion point is in the scalp at a point distal from the frontal hairline; and the suture is pushed through the reticular dermis underneath the scalp until the first end of the suture passes through the frontal hairline, extending to be proximate to the browline.

Other embodiments are provided for a method for joining and holding closed an axial wound in a blood vessel such as an artery or vein, using an insertion device. The first pointed end of the suture and the leading end of the insertion device are inserted through an entry point in the tissue spaced from and on one side of the wound. The first end of the suture and leading end of the insertion device are pushed through the tissue until penetrating the blood vessel wall on one side of the wound, continuing until extending into the interior of the blood vessel. The first end of the suture and leading end of the insertion device are then pushed through the interior of the blood vessel until the first end of the suture and the leading end of the insertion device penetrate the blood vessel wall on the other side of the wound, continuing through the blood vessel wall and penetrating the tissue on the other side of the wound. The first end of the suture and leading end of the insertion device are pushed through the tissue. In one embodiment, the second axial location is disposed in the blood vessel wall on one side of the wound and the first axial location is disposed in the blood vessel wall on the other side of the wound, resulting in no barbs being disposed in the interior of the blood vessel. The insertion device is gripped and pulled at the trailing end for removal, leaving the suture in place, and the tissue may be advanced on the two sides of the wound together as necessary to close the wound.

BRIEF DESCRIPTION OF THE DRAWINGS

For a more complete understanding of the present invention, reference should now be had to the embodiments shown in the accompanying drawings and described below. In the drawings:

FIG. 1 is a perspective view of an embodiment of a barbed suture with straight pointed ends for use according to the methods of the present invention;

FIG. 2 is a perspective view of a barbed suture with curved pointed ends for use according to the methods of the present invention;

FIG. 23 is a side elevation view of a finger with a portion of the outer layer of tissue cut-away to schematically show a severed tendon;

FIG. 24 is a plan view of the Kessler method for joining two ends of a severed tendon;

FIGS. 25-28 are perspective views of an embodiment of a method according to the present invention for joining two ends of a severed tendon;

DESCRIPTION

Figure 3:
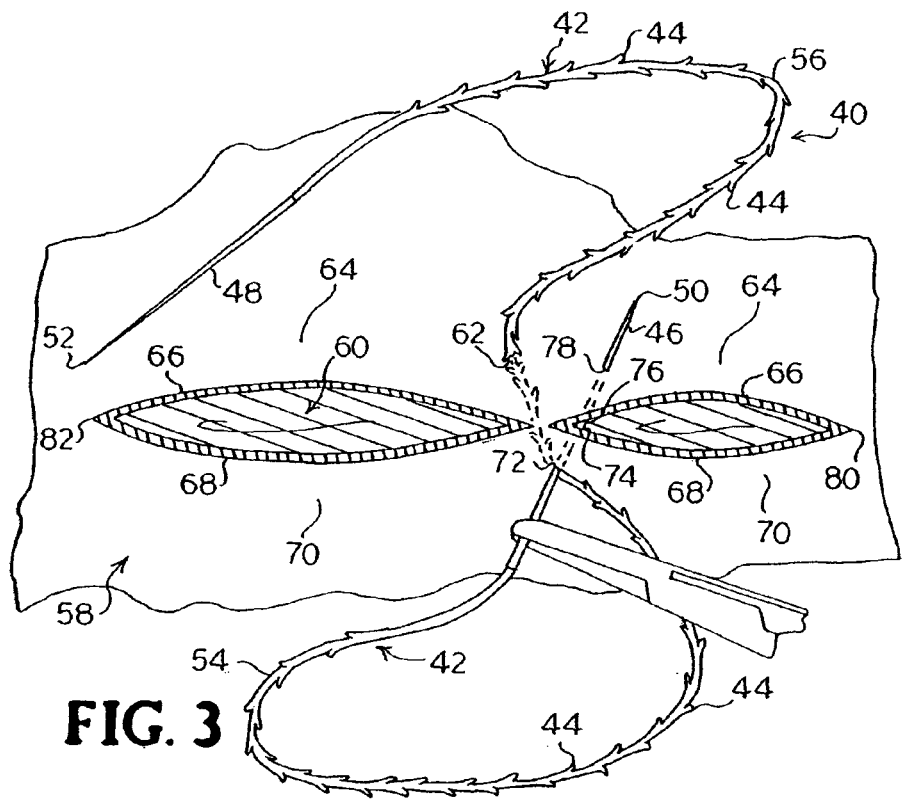
FIGS. 3-6 are plan views of an embodiment of a method according to the present invention for joining two sides of an open wound in tissue.

As used herein, the term "wound" means a surgical incision, cut, laceration, severed tissue or accidental wound in human skin or other bodily tissue, or other condition where suturing, stapling, or the use of another tissue connecting device might be required.

As used herein, the term "tissue" includes tissues such as skin, bone, muscle, organs, and other soft tissue such as tendons, ligaments and muscle.

Certain other terminology is used herein for convenience only and is not to be taken as a limitation on the invention. For example, words such as "upper," "lower," "left," "right," "horizontal," "vertical," "upward," and "downward" merely describe the configuration shown in the figures. It is understood that the components may be oriented in any direction and the terminology, therefore, should be understood as encompassing such variations unless specified otherwise.

Referring now to the drawings, wherein like reference numerals designate corresponding or similar elements throughout the several views, there is shown in FIGS. 1 and 2 a suture for use according to the present invention and generally designated at 40. The suture 40 includes an elongated body 42 having a plurality of barbs 44 disposed along the length of the body 42. First and second ends 46, 48 of the body 42 terminate in points 50, 52 for penetrating tissue.

The body 42 of the suture 40 is, in one embodiment, circular in cross section. Suitable diameters for the body 42 of the suture 40 range from about 0.001 mm to about 1.0 mm. The body 42 of the suture 40 could also have a non-circular cross-sectional shape which would increase the surface area of the body 42 and facilitate the formation of multiple barbs 44.

The length of the suture 40 can vary depending on several factors such as the extent of the wound to be closed, the type of tissue to be joined, the location of the wound, and the like. A suture 40 of proper length is selected for achieving suitable results in a particular application.

Material for the body 42 of the suture 40 is available in a wide variety of monofilament suture material. The particular suture material chosen depends on the strength and flexibility requirements. In one embodiment, the material for the body 42 is flexible and substantially nonresilient so that the shape of an inserted suture 40 will be determined by the path of insertion and the surrounding tissue. In some applications, however, it may be desirable for at least a portion of the body 42 to have sufficient dimensional stability to assume a substantially rigid configuration during use and sufficient resiliency to return to a predetermined position after deflection therefrom. The portions of the ends 46, 48 of the suture 40 adjacent the points 50, 52 may be formed of a material sufficiently stiff to enable the points 50, 52 to penetrate tissue in which the suture 40 is used when a substantially axial force is applied to the body 42. Variations in surface texture of the body 42 of the suture 40 can impart different interaction characteristics with tissues.

The body 42 can be formed of a bioabsorbable material which allows the suture 40 to be absorbed over time into the tissue as the wound heals. Bioabsorbable material is particularly useful in arthroscopic surgery and methods of suturing. Many compositions useful as bioabsorbable materials can be used to make the body 42 of the suture 40 for use in the methods of the present invention. Generally, bioabsorbable materials are thermoplastic polymers. Selection of the particular material is determined by the desired absorption or degradation time period which depends upon the anticipated healing time for the subject of the procedure. Biodegradable polymers and co-polymers range in degradation time from about one month to over twenty-four months. They include, but are not limited to, polydioxanone, polylactide, polyglycolide, polycaprolactone, and copolymers thereof. Other copolymers with trimethylene carbonate can also be used. Examples are PDS II (polydioxanone), Maxon (copolymer of 67% glycolide and 33% trimethylene carbonate), and Monocryl (copolymer of 75% glycolide and 25% caprolactone). Germicides can also be incorporated into the body 42 of the suture 40 which are retained by the suture 40 to provide long lasting germicidal properties.

The body 42 of the suture 40 can also be formed from non-absorbable material such as nylon, polyethylene terephthalate (polyester), polypropylene, and expanded polytetrafluoroethylene (ePTFE). Alternatively, the suture body 42 can also be formed of metal (e.g. steel), metal alloys, plastic, or the like.

The plurality of barbs 44 is axially-spaced along the body 42 of the suture 40. The barbs 44 are oriented in one direction facing toward the first end 46 of the suture 40 for a first portion 54 of the length of the suture and in an opposite direction facing the second end 48 of the suture 40 for a second portion 56 of the suture. The barbs 44 are yieldable toward the body 42. The barbs 44 on each portion 54, 56 of the suture are oriented so as to allow movement of the suture 40 through the tissue in one direction along with the corresponding end 46, 48 of the suture 40. The barbs 44 are generally rigid in an opposite direction to prevent the suture 40 from moving in the tissue in the opposite direction.

The barbs 44 can be arranged in any suitable pattern, for example, in a helical pattern as shown in FIGS. 1 and 2. The number, configuration, spacing and surface area of the barbs 44 can vary depending upon the tissue in which the suture 40 is used, and depending on the composition and geometry of the suture body. The proportions of the barbs 44 may remain relatively constant while the overall length of the barbs 44 and the spacing of the barbs 44 are determined by the tissue being connected. For example, if the suture 40 is intended to be used to connect the edges of a wound in skin or tendon, the barbs 44 can be made relatively short and more rigid to facilitate entry into this rather firm tissue. If the suture 40 is intended for use in fatty tissue, which is relatively soft, the barbs 44 can be made longer and spaced farther apart to increase the holding ability in the soft tissue. Moreover, the ratio of the number of barbs 44 on the first portion 54 of the suture 40 to the number of barbs 44 on the second portion 56, and the lengths of each portion 54, 56, can vary depending on the application and needs.

The surface area of the barbs 44 can also vary. For example, fuller-tipped barbs 44 can be made of varying sizes designed for specific surgical applications. For joining fat and relatively soft tissues, larger barbs 44 are desired, whereas smaller barbs 44 are more suited for collagen-dense tissues. There are also situations where a combination of large and small barbs 44 within the same structure will be beneficial such as when a suture 40 is used in tissue repair with differing layer structures. Use of the combination of large and small barbs 44 with the same suture 40 wherein barb 44 sizes are customized for each tissue layer will ensure maximum anchoring properties.

The barbs 44 may be formed on the surface of the body 42 according to any suitable method, including cutting, molding, and the like. The preferred method is cutting with acute angular cuts directly into the suture body 42 with cut portions pushed outwardly and separated from the body 42 of the suture 40. The depth of the barbs 44 formed in the suture body 42 depends on the diameter of the suture material and the depth of cut. A particularly suitable device for cutting a plurality of axially spaced barbs 44 on the exterior of suture filaments utilizes a cutting bed, a cutting bed vise, a cutting template, and a blade assembly to perform the cutting. When operated, the cutting device has the ability to produce a plurality of axially spaced barbs 44 in the same or random configuration and at different angles in relation to each other. Various other suitable methods of cutting the barbs 44 have been proposed including the use of a laser. The barbs 44 could also be cut manually. However, manually cutting the barbs 44 is labor intensive, decreases consistency, and is not cost effective. The suture 40 could also be formed by injection molding, extrusion, stamping and the like. The suture 40 can be packaged in any number of desired pre-cut lengths and in pre-shaped curves.

The ends 46, 48 of the suture 40 may be straight (FIG. 1) or curved (FIG. 2). In one embodiment, the ends 46, 48 of the suture 40 may be surgical needles secured at each end of the body 42 of the suture 40 so that the body 42 extends between the shank ends of the two needles. The needles are preferably constructed of stainless steel or other surgical grade metal alloy. The needles may be secured to the suture body 42 by means of adhesives, crimping, swaging, or the like, or the joint may be formed by heat shrinkable tubing. A detachable connection may also be employed such that the needles may be removed from the body 42 of the suture 40 by a sharp tug or pull or by cutting. The length of the needles is selected to serve the type of tissue being repaired so that the needles can be completely removed leaving the suture body 42 in the desired position within the tissue.

Barbed sutures suitable for use according to the methods of the present invention are described in U.S. Pat. No. 5,342, 376, entitled "Inserting Device for a Barbed Tissue Connector", U.S. Pat. No. 6,241,747, entitled "Barbed Bodily Tissue Connector", and U.S. Pat. No. 5,931,855. The contents of U.S. Pat. No. 5,342,376, U.S. Pat. No. 6,241,747, and U.S. Pat. No. 5,931,855 are hereby incorporated by reference.

According to the present invention, a surgical procedure using barbed sutures 40 is provided for binding together living tissue for healing and regrowth or reconfiguration in vivo. In general, when the suture 40 is used in tissue to repair a wound, the suture is passed through tissue at each of the sides of the wound. The point 50 at one end 46 of the suture 40 is inserted into a first side of a wound such that the point 50 pierces the tissue and the barbs 44 on the end portion 54 of the suture 40 corresponding to the one end 46 yield toward the body 42 to facilitate movement of the suture 40 through the tissue in the direction of insertion. The other end 48 of the suture 40 is also inserted into a side of the wound and advanced through the tissue in like manner. The sides or faces of the wound are then moved together along the suture portions 54, 56 within the tissue to close the wound. The barbs 44 of the suture 40 grasp the surrounding tissue on each side of the wound and maintains the edges of the wound in position during healing. The leading ends 46, 48 of the suture 40 protruding from the tissue are then cut and discarded. In one embodiment, ends of the suture 40 in the tissue are made to lie below the surface of the skin by first depressing the skin immediately around the ends and severing the suture body 42 closely against the skin. The skin will rise to cover the ends of the suture 40.

FIGS. 3-6 show a section of tissue including a portion of a patient's skin 58 and subcutaneous tissue defining a wound 60 from the surface of the skin 58 down into the tissue. It is understood that the wound 60 in the tissue can be of any configuration and from any anatomical part or organ of the body. Accordingly, depending on the configuration of the wound, the wound may comprise several sides and faces. However, the wounds depicted in the figures are straight incisions in the skin 58 to reduce the complexity of the description of the method of the present invention. It is understood that the applicants do not intend to limit the method of the present invention to the closure of only straight incisions.

In this embodiment of the method of the present invention, the user, such as a surgeon, selects a suture 40 of sufficient length and having straight ends 46, 48. As noted above, in one embodiment, the ends 46, 48 may be surgical needles.

Referring to FIG. 3, the surgeon inserts the needle 46 at the end of the first portion 54 of the suture 40 into the tissue at a point 62 on a first side 64 of the wound 60 and laterally spaced from the face 66 of the wound 60 at the first side 64. The surgeon advances the needle 46 along a selected substantially straight path through the tissue to extend out of the tissue at a subcutaneous point (not shown) in the first face 66 of the wound 60 and subcutaneously penetrating a point (not shown) in a face 68 of a second side 70 of the wound 60. The surgeon continues to advance the needle 46 through the tissue until the point 50 of the needle emerges from the tissue at a distal end of the selected path at an exit point 72 on the second side 70 of the wound 60. The exit point is laterally spaced from the face 68 of the second side 70 of the wound and longitudinally spaced in a first direction from the point of insertion 62 at the first side 64 of the wound 60. The surgeon grips the exposed portion of the needle 46 and pulls the needle 46 out of the tissue. This action draws the first portion 54 of the suture 40 having barbs 44 for resisting movement in the opposite direction through the tissue until the barbs 44 on the second portion 56 engage the surface of the skin 58 at the insertion point 62 preventing further advancement of the suture 40 through the tissue. A length of the first portion 54 of the suture body 42 is thus positioned in the tissue along the selected path. The faces 66, 68 of the wound 60 are approximated by pushing the adjacent sides 64, 70 of the tissue together along the first portion 54 of the body 42 of the suture 40 in the tissue.

The needle 46 is next inserted into the tissue at the exit point 72 and advanced along a substantially straight path through the tissue to extend out of the tissue at a subcutaneous point 74 in the second face 68 of the wound 60 and subcutaneously penetrating a point 76 in the first face 66 of the wound 60. The surgeon continues to advance the needle 46 through the tissue until the point end 50 emerges from the tissue at a distal end of the selected path at an exit point 78 on the first side 64 of the wound 60 that is laterally spaced from the first face 66 and longitudinally spaced in the first direction from the point of insertion 72 at the second side 70 of the wound 60. Again the surgeon grips the exposed portion of the needle 46 and pulls the needle 46 out of the tissue, drawing the first portion 54 of the suture 40 through the tissue.

Figure 4:
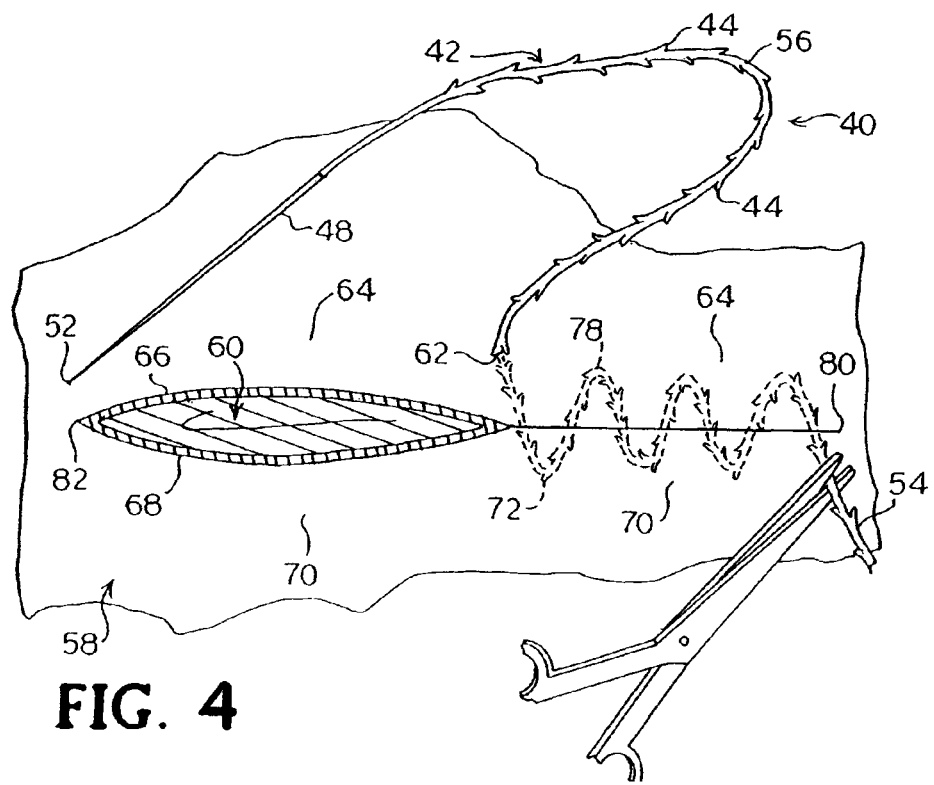

The previous steps are repeated with the first portion 54 of the suture 40 by inserting the needle 46 into the exit point 78 on the first side 64 of the wound 60 for advancing longitudinally in the first direction along the wound 60 in a "zigzag" pattern as shown in FIG. 4. The number of passes of the needle 46 is chosen in accordance with the size of the wound 60 and the strength required to hold the wound closed. The remaining length of the first portion 54 of the suture 40 protruding from the tissue at a first end 80 of the wound 60 is cut and discarded, leaving the remaining first portion 54 of the suture 40 in the tissue. The faces 66, 68 of the wound 60 are approximated by pushing the adjacent sides 64, 70 of the tissue together along the body 42 of the suture 40 in the tissue.

It is understood that the step of approximating the sides 64, 70 of the wound 60 can be performed as the suture 40 is advanced or after the end 80 of the wound 60 is reached. Moreover, we do not intend to limit ourselves to the depth of the suture paths shown in the FIGs. as the depth of the suture paths may be determined by the surgeon or the wound to be closed. Further, it is understood that straight ends 46, 48 of the suture may also produce more curved transitions as determined by the surgeon.

Figure 5:
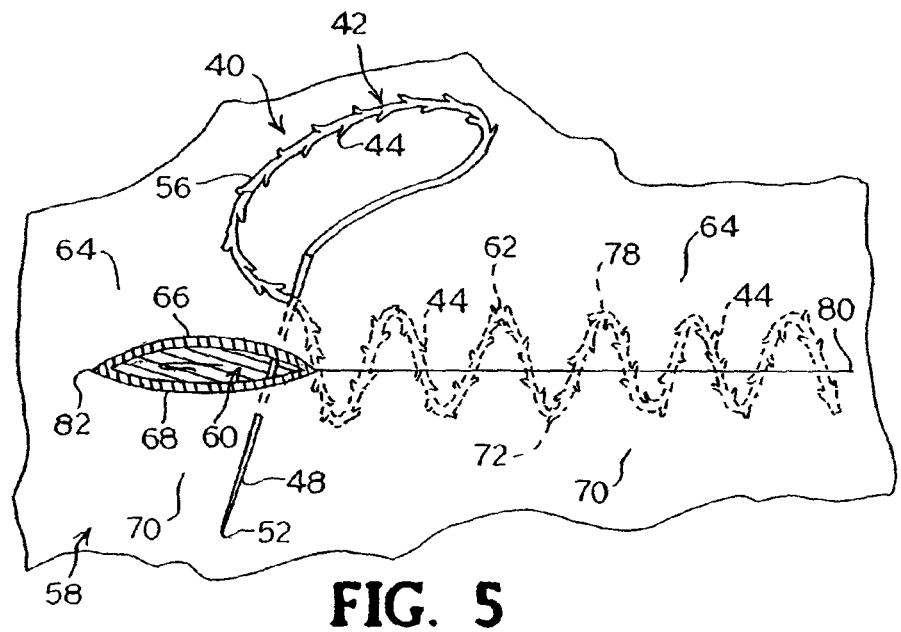
Figure 6:
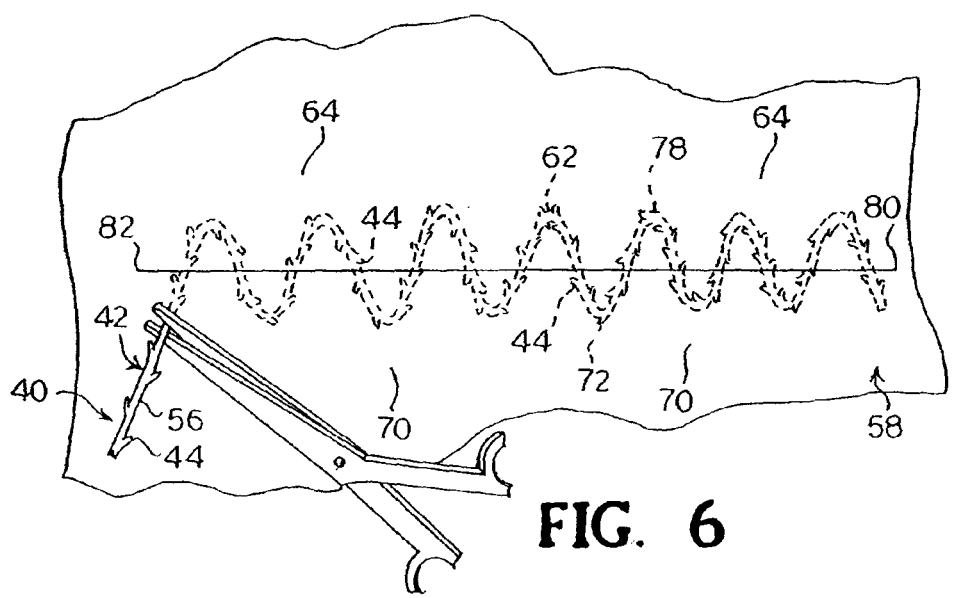

The surgeon repeats the steps of this procedure with the second needle 48 on the second portion 56 of the suture (FIG. 5). The initial insertion point 62 of the second needle 48 is at the same initial point of insertion 62 of the first needle 46 at the first side 64 of the wound 60. The surgeon thus advances the second portion 56 of the suture 40 into the tissue along the wound 60 in a direction toward the other end 82 of the wound 60 using the same zigzag pattern approximating the faces 66, 68 of the wound 60. The remaining length of the second portion 56 of the suture 40 protruding from the skin 58 at the end 82 of the wound 60 is then cut and discarded (FIG. 6).

An embodiment of the method for joining the sides of an open wound in tissue according to the present invention using a subcuticular stitch is shown in FIGS. 7-10. The tissue shown in the figures includes an epidermis 84, dermis 86, fat 88, fascia 90 and muscle 92. By penetrating the subcutaneous layers only and not the outer skin 58 layer, a wound 60 can be closed to facilitate healing while minimizing scar tissue.

Figure 7:
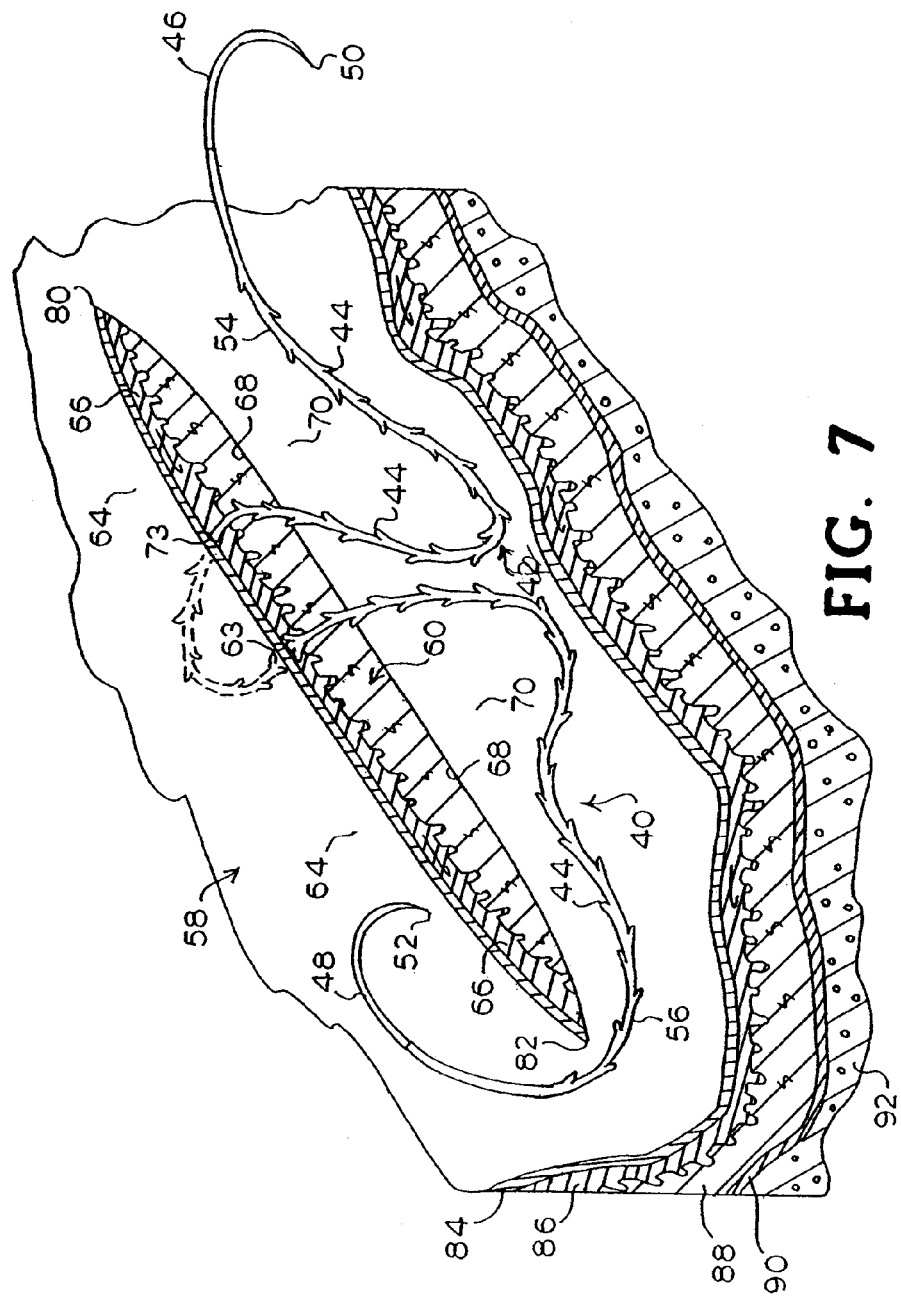
FIGS. 7-10 are perspective views of another embodiment of a method according to the present invention for joining two sides of an open wound in tissue.

Referring to FIG. 7, the subcuticular stitch method of the present invention uses a barbed suture 40 including curved ends 46, 48. The surgeon begins by inserting the first needle 46 into the tissue below the skin 58 surface at a face 66 on a first side 64 of the wound 60 at an initial insertion point 63 longitudinally spaced from the ends 80, 82 of the wound 60. The surgeon advances the needle 46 through the tissue along a curvilinear path until the point 50 of the needle 46 extends from the tissue at a subcutaneous exit point 73 in the first face 66 of the wound 60 longitudinally spaced toward one end 80 of the wound from the entry point 63 of the needle 46. The surgeon grips the needle 46 and pulls the needle 46 out of the tissue, drawing the first portion 54 of the suture 40 through the tissue until the barbs 44 on the second portion 56 engage the tissue at the insertion point 63 preventing further advancement of the suture 40 through the tissue. A length of the first portion 54 of the suture body 42 is thus positioned in the tissue along the selected curvilinear path as seen in FIG. 7.

Figure 8:
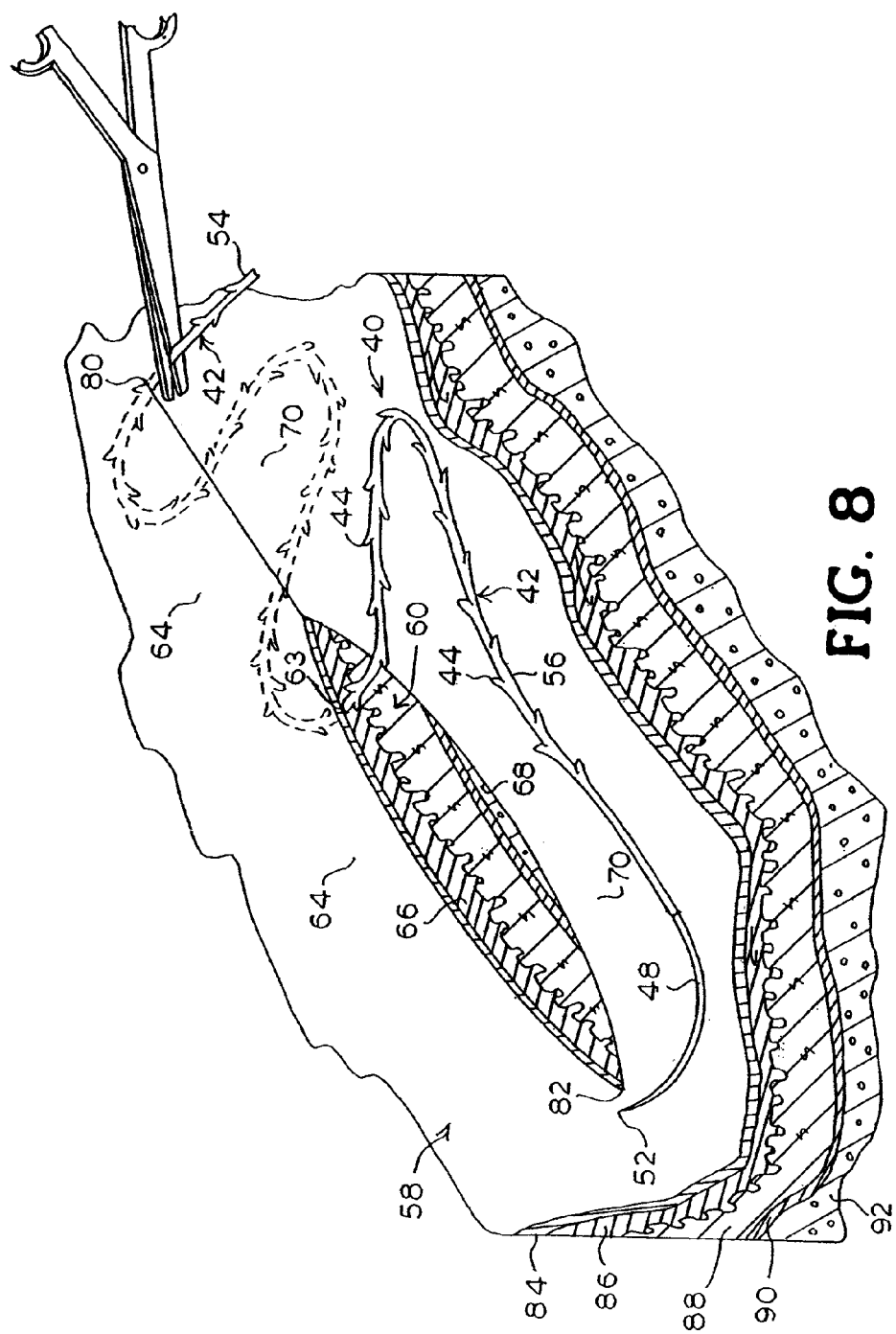

Turning to FIG. 8, the surgeon then inserts the needle 46 into the tissue at a subcutaneous entry point (not shown) in the face 68 at the second side 70 of the wound 60. The surgeon repeats the above steps of pushing the needle 46 through the tissue along a selected curvilinear path so that the point 50 of the needle 46 emerges from a subcutaneous exit point (not shown) in the second face 68 of the wound 60 longitudinally spaced toward the end 80 of the wound 60 from the entry point. The surgeon grips the needle 46 and draws the first portion 54 of the suture 40 into the tissue further along the wound 60. In this manner, the surgeon advances the first portion 54 of the suture 40 longitudinally along the wound 60 to the one end 80 of the wound in a wave-like or "sinusoidal" pattern. As noted above, the faces 66, 68 of the wound 60 are approximated as the surgeon progresses, or when the end 80 of the wound 60 is reached, by pushing the adjacent sides 64, 70 of the tissue together along the body 42 of the suture 40. The needle 46 along with remaining length of the first portion 54 of the suture 40 is drawn through the surface of the skin 58 at the one end 80 of the wound 60 is cut and discarded (FIG. 8).

Figure 9:
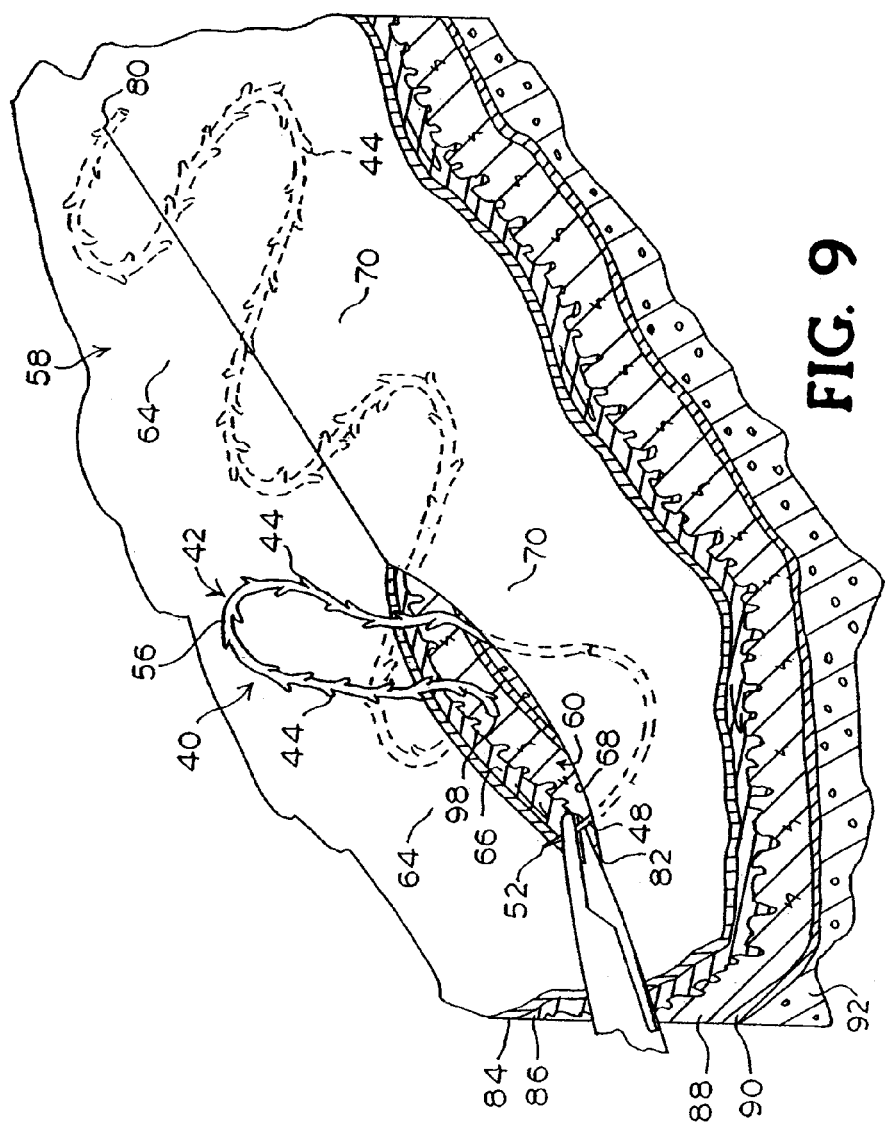
Figure 10:
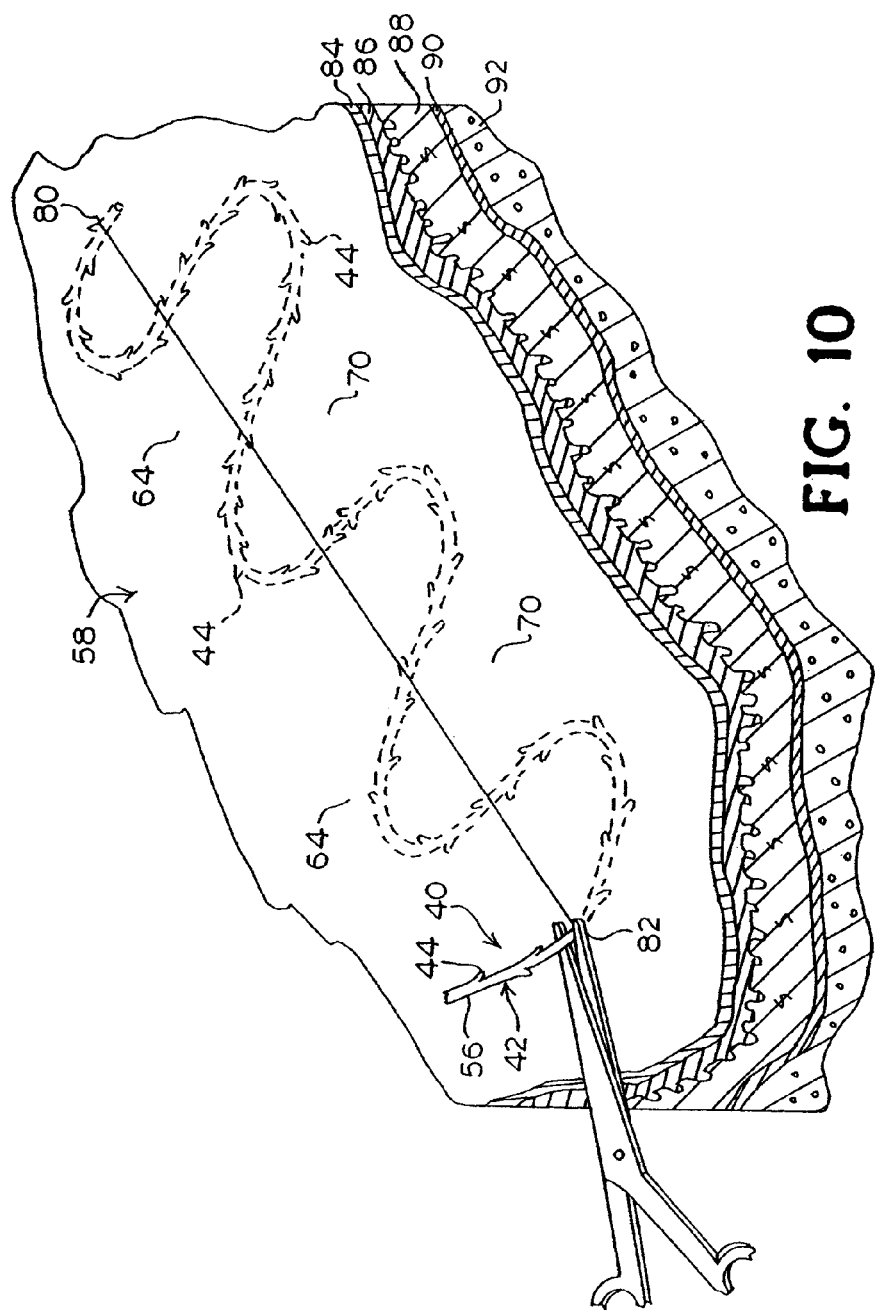

The surgeon repeats the procedure at the other end of the wound (FIG. 9) with the second portion 56 of the suture 40. The surgeon begins by inserting the second needle 48 into the tissue at a subcutaneous point (not shown) in the second face 68 of the wound 60. The surgeon advances the second needle 48 along a curvilinear path from the point of initial insertion toward the other end 82 of the wound 60 until the needle 48 emerges from a subcutaneous exit point (not shown) the second face 68 of the wound 60 longitudinally spaced from the initial entry point of the needle 48. The surgeon then pulls the needle 48 from the tissue, drawing the second portion 56 of the suture 40 into the tissue, and inserts the needle 48 into the first face 66 of the wound 60 at a subcutaneous entry point (not shown) at the first side 64 of the wound 60. Again, the surgeon advances the needle 48 along a curvilinear path until the needle 48 emerges from a subcutaneous exit point 98 in the face 66 further toward the other end 82 of the wound and draws the needle 48 and suture portion 56 through the tissue. FIG. 9 shows the needle 48 being drawn a second time from the second face 68 of the wound 60. Thus, the surgeon advances the second portion 56 of the suture in a sinusoidal pattern to the end 82 of the wound 60 (FIG. 10) and approximates the faces 66, 68 of the wound 60. The length of the second portion 56 of the suture body 42 protruding from the skin 58 at the end of the wound 60 is then cut and discarded.

Figure 11:
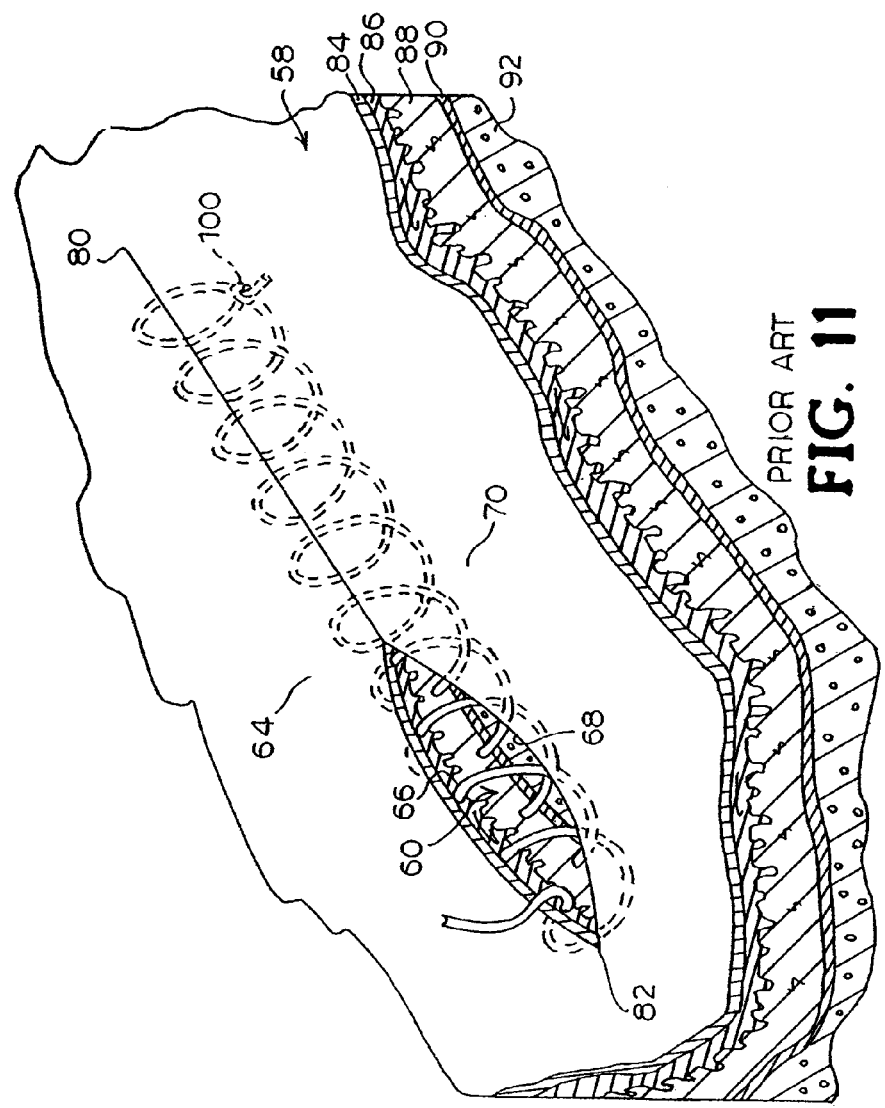
FIG. 11 is a perspective view of a prior art method for joining two sides of an open wound in tissue using a spiraling suture path.

FIG. 11 shows a prior art subcutaneous suturing method for closing a wound 60 using a spiraling, "corkscrew-shaped" stitch pattern. The surgeon begins at one end 80 of the wound by tying a knot 100 in the first loop and advancing the suture in a corkscrew pattern to the other end of the wound 82 where the suture is tied off. Tying the knots at the end and burying them, which is preferred by the surgeon, is technically very challenging, even more so when the incision is almost closed.

FIGS. 12-15 show a similar corkscrew-shaped stitch pattern for closing a wound 60 according to an embodiment of the method of the present invention. This embodiment is similar to the method described above using a subcutaneous sinusoidal stitch pattern.

Figure 12:
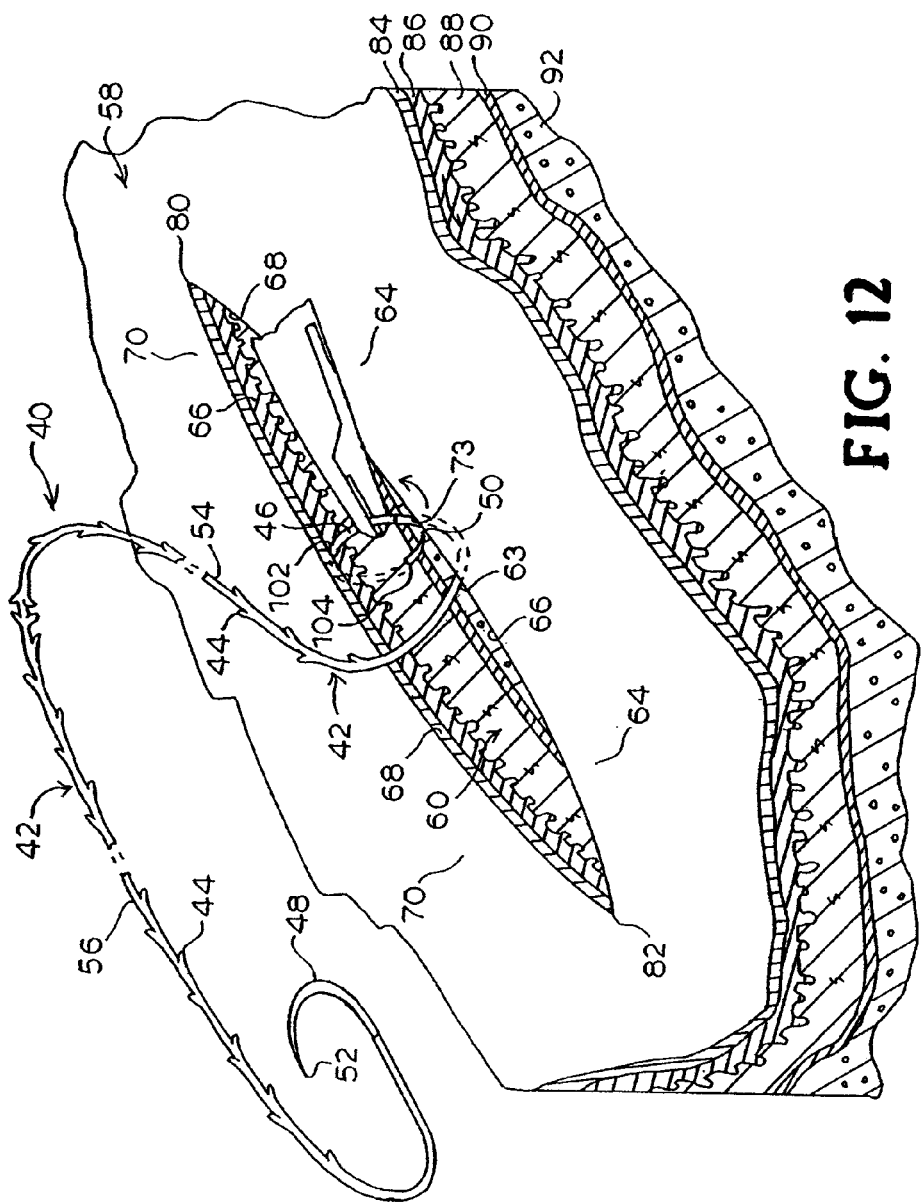
FIGS. 12-15 are perspective views of an embodiment of a method according to the present invention for joining two sides of an open wound in tissue using a spiraling suture path.
Figure 13:
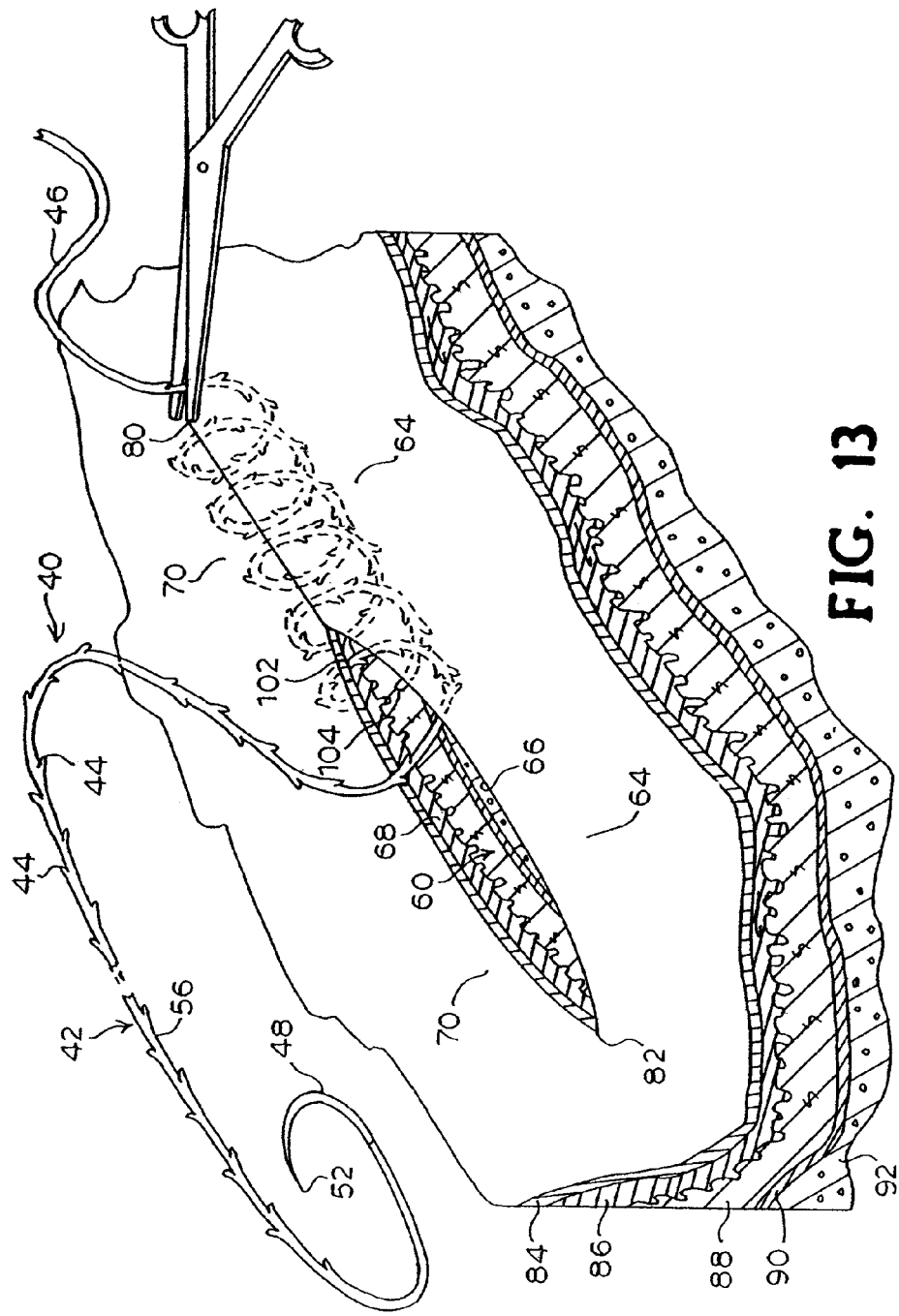

Referring to FIG. 12, the surgeon begins by inserting one of the needles 46 into the tissue below the skin 58 surface at a face 66 on a first side 64 of the wound 60 at an initial subcutaneous insertion point 63 longitudinally spaced from the ends 80, 82 of the wound 60. The surgeon advances the needle 46 upward through the tissue along a curvilinear path until the point 50 of the needle 46 extends from the tissue at a subcutaneous exit point 73 in the first face 66 of the wound 60 longitudinally spaced toward one end 80 of the wound and above the entry point 63 of the needle 46. The surgeon then inserts the needle 46 into the tissue at a subcutaneous entry point 102 in the face 68 at the second side 70 of the wound 60. The surgeon pushes the needle 46 through the tissue along a selected curvilinear path so that the point 50 of the needle 46 emerges from a subcutaneous exit point 104 in the second face 68 of the wound 60 longitudinally spaced toward the end 80 of the wound 60 and below the entry point 102. The surgeon repeats these steps (FIG. 13) for advancing the first portion 54 of the suture 40 longitudinally along the wound 60 to the one end 80 of the wound in the spiraling, corkscrew stitch pattern. It is understood that the number and diameter of coils can be varied as desired. At any selected convenient point, the surgeon grips the needle 46 for drawing the first portion 54 of the suture 40 through the tissue until the barbs 44 on the second portion 56 engage the tissue at the insertion point 63 preventing further advancement of the suture 40 through the tissue. The surgeon approximates the faces 66, 68 of the wound 60 as the surgeon progresses or when the end 80 of the wound 60 is reached as described above. The remaining length of the first portion 54 of the suture 40 is drawn through the surface of the skin 58 at the one end 80 of the wound 60 and cut and discarded.

Figure 14:
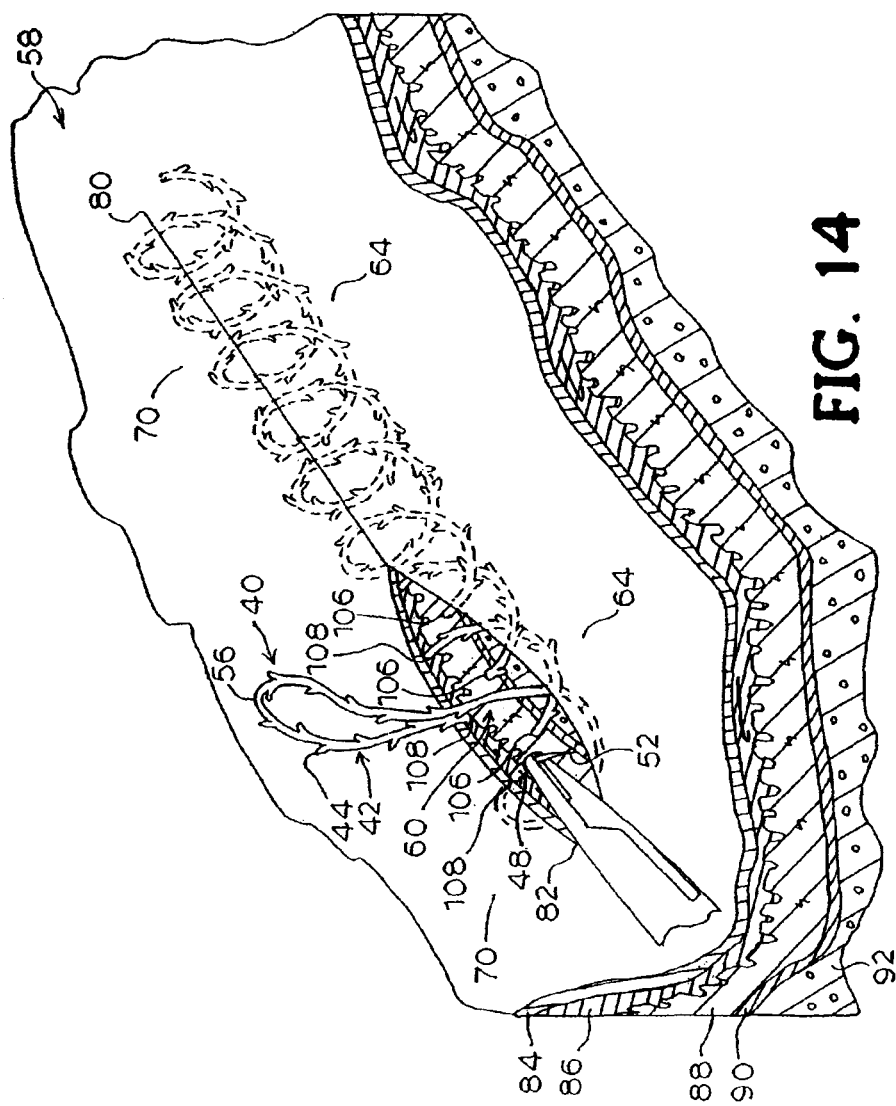
Figure 15:
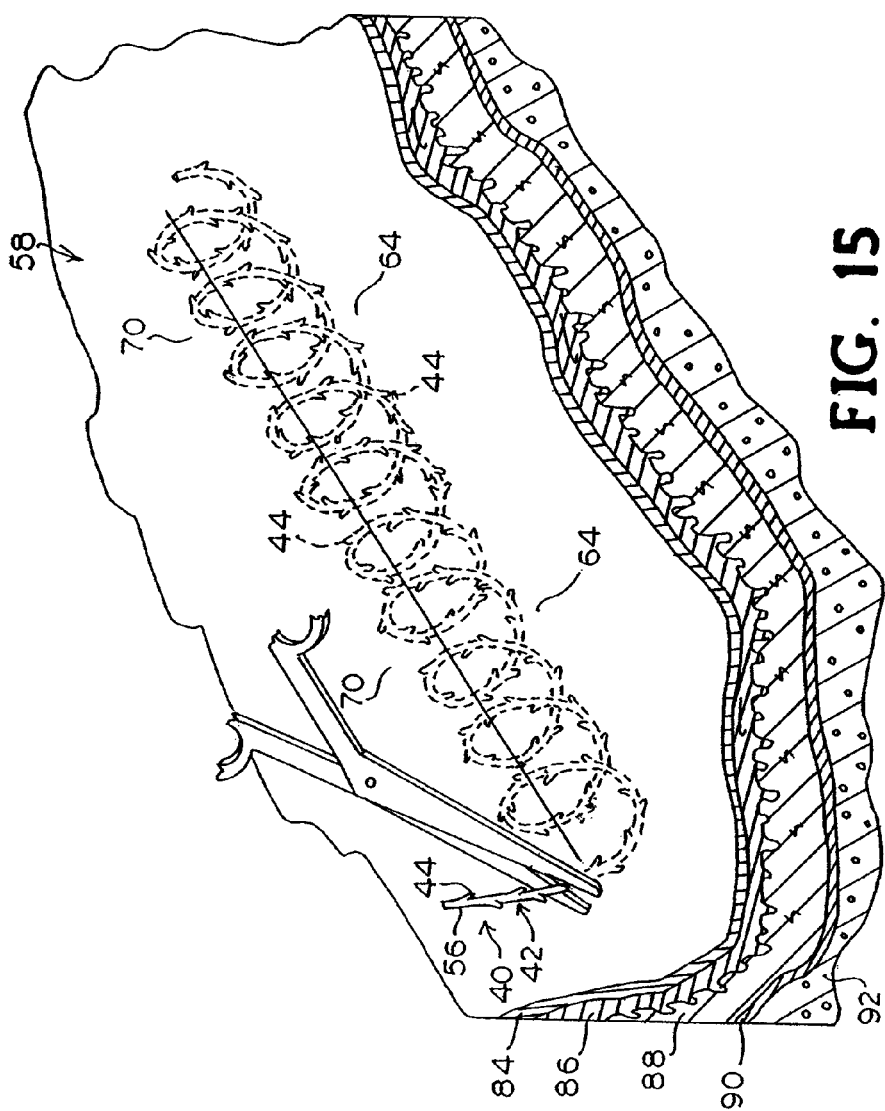

The surgeon repeats the procedure at the other end 82 of the wound 60 with the second portion 56 of the suture 40. As seen in FIG. 14, several "coils" of the second portion 56 of the suture 40 have been entered into the tissue in a direction toward the other end 82 of the wound 60. Subcutaneous entry points 106 and exit points 108 in the faces 66, 68 of the wound 60 are visible. The surgeon advances the second portion 56 of the suture 40 to the end 82 of the wound 60 (FIG. 15) and approximates the faces 66, 68 of the wound 60. The length of the second portion 56 of the suture body 42 protruding from the skin 58 at the end of the wound 60 is then cut and discarded.

Figure 16:
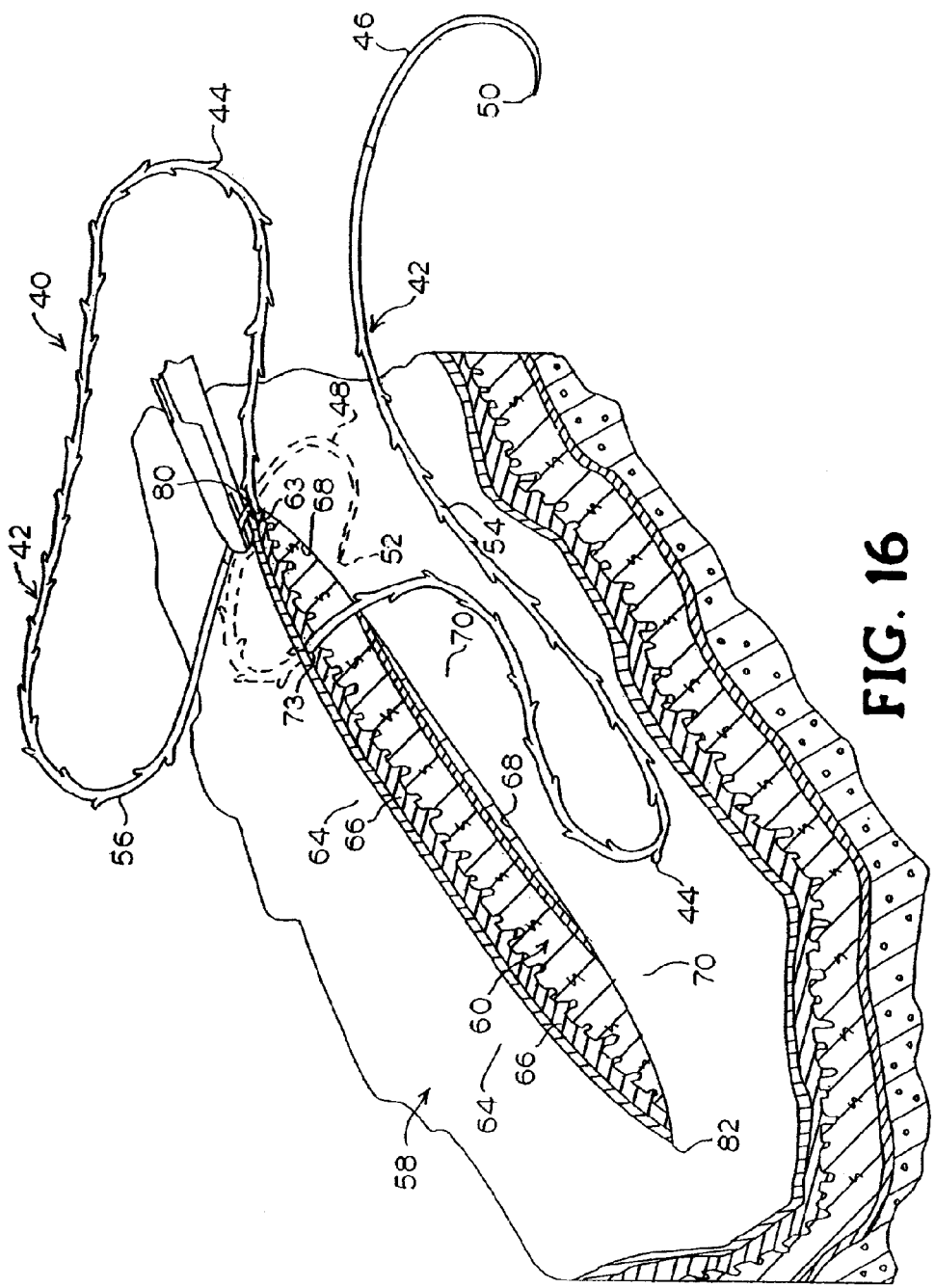
FIGS. 16-18 are perspective views of still another embodiment of a method according to the present invention for joining two sides of an open wound in tissue.
Figure 17:
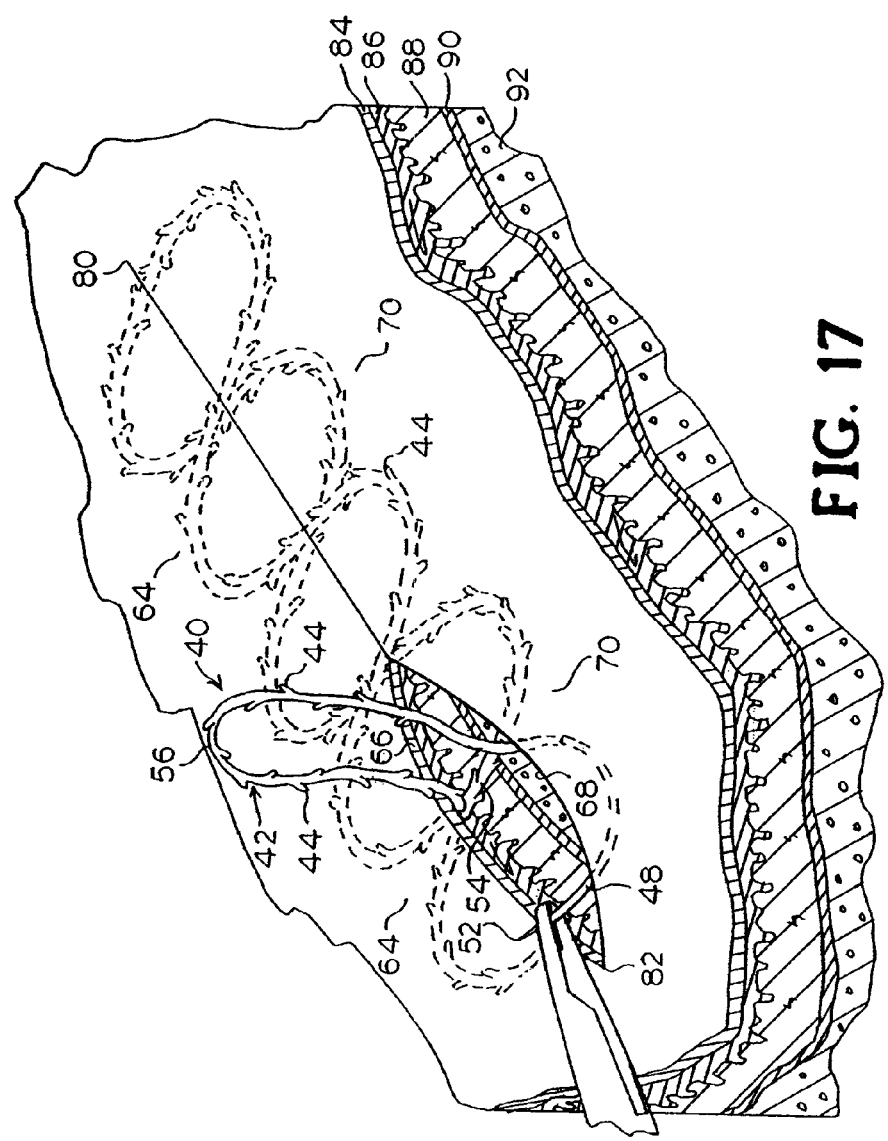
Figure 18:
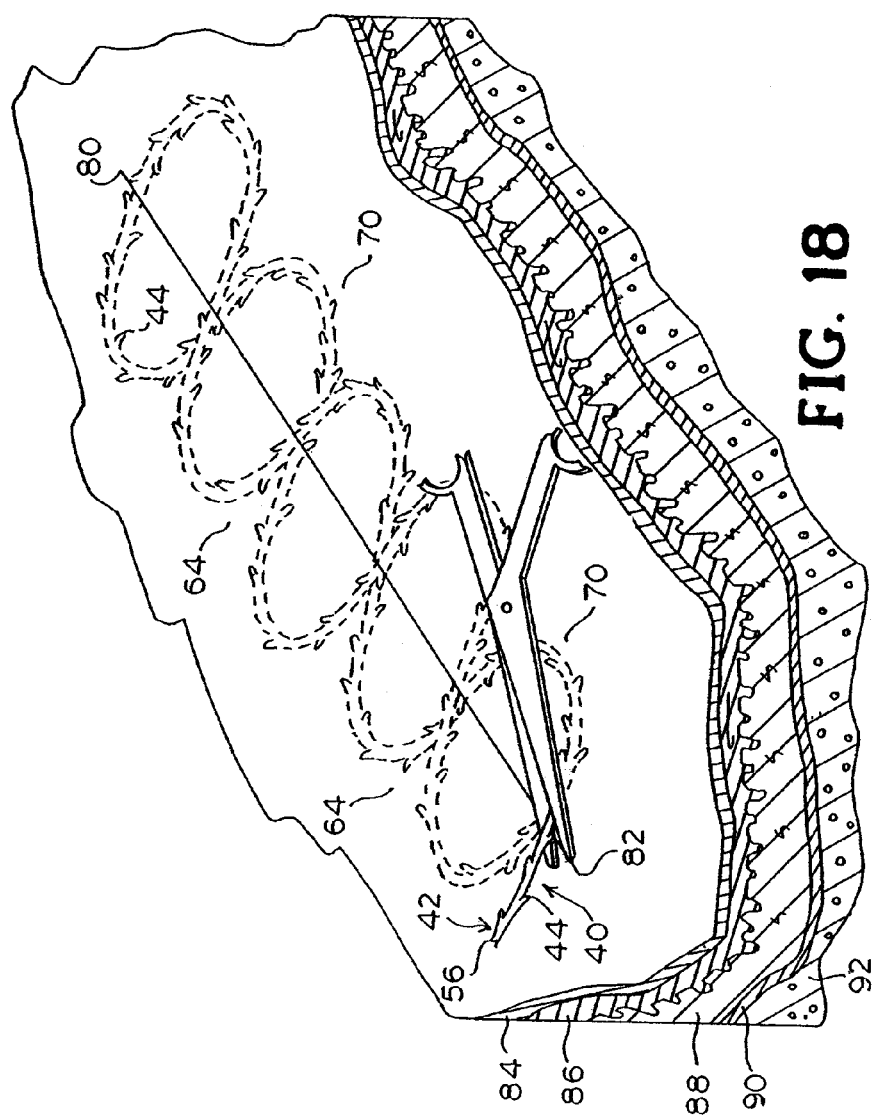

Another embodiment of a subcutaneous suturing method for joining and holding closed an open wound 60 in tissue according to the present invention is shown in FIGS. 16-18. This method also uses a barbed suture 40 having curved pointed ends 46, 48, such as surgical needles.

Referring to FIG. 16, the surgeon begins by inserting the first needle 46 subcutaneously into the tissue at a face 66 on a first side 64 of the wound 60 at an initial insertion point 63 adjacent one end 80 of the wound 60 and pushes the needle 46 through the tissue along a selected curvilinear path until the needle 46 extends from the tissue at a subcutaneous exit point 73 in the first face 66 of the wound 60 longitudinally spaced from the end 80 of the wound 60 in a direction toward the other end 82 of the wound 60. The surgeon grips the needle 46 and pulls the needle 46 out of the tissue for drawing the first portion 54 of the suture 40 including barbs 44 for resisting movement in the opposite direction through the tissue until the barbs 44 of the second portion 56 engage the first face 66 of the wound 60 at the insertion point 63 preventing further advancement of the suture 40 into the tissue. A length of the first portion 54 of the suture body 42 is thus positioned in the tissue along the selected curvilinear path.

As further seen in FIG. 16, the surgeon next inserts the second surgical needle 48 into the tissue at a subcutaneous entry point (not shown) in the face 68 at the second side 70 of the wound 60 substantially opposite the initial point of insertion 63 of the first needle 46 at the one end 80 of the wound 60. The surgeon advances the second needle 48 through the tissue along a selected curvilinear path until the needle 48 extends from the tissue at a subcutaneous exit point (not shown) in the second face 68 of the wound 60. The surgeon then pulls the second needle 48 for drawing the second portion 56 of the suture 40 through the tissue, including barbs 44 for resisting movement in the opposite direction, leaving a length of the second portion 56 of the suture 40 in the tissue at the end 80 of the wound 60.

The surgeon repeats the above steps with the first needle 46 and second needle 48 at the second and first sides 64, 70, respectively, of the wound 60. In this manner, the surgeon advances the suture 40 longitudinally along the wound 60 from the one end 80 of the wound to the other 82 in a "shoe-lace" pattern. As seen in FIG. 17, several passes of the suture 40 have been entered into the tissue of the wound 60. The faces 66, 68 of the wound 60 are approximated as the surgeon progresses, or when the end 82 of the wound 60 is reached, by pushing the adjacent sides 64, 70 of the tissue together along the body 42 of the suture 40. The lengths of the first portion 54 and second portion 56 of the suture 40 protruding from the skin 58 are cut and discarded (FIG. 18).

It is understood that the method of the present invention shown in FIGS. 7-10 can be used to generate a similar stitch pattern if a second suture is used which is entered in the tissue to mirror the path of the first suture.

Figure 19:
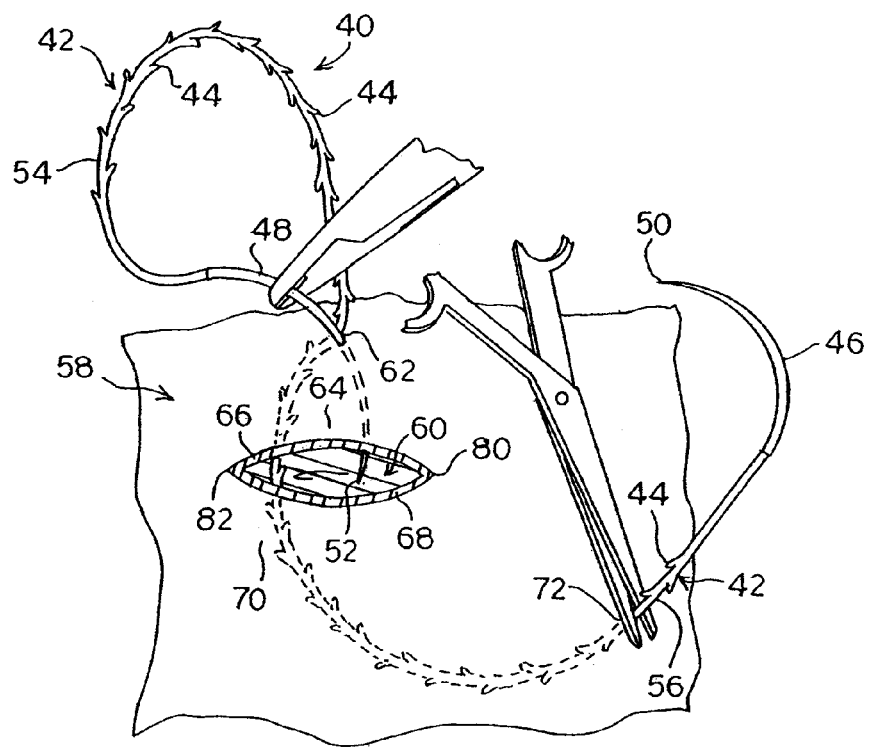
FIGS. 19 and 20 are plan views of a further embodiment of a method according to the present invention for joining two sides of an open wound in tissue.
Figure 20:
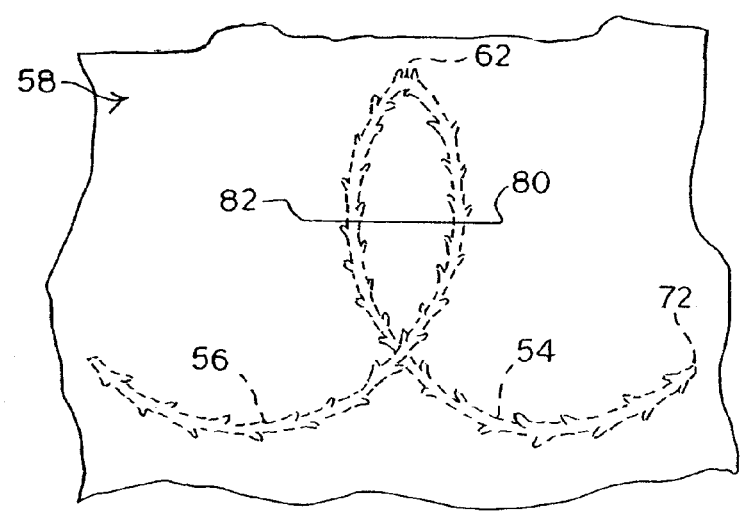

Another embodiment of the method according to the present invention for joining the sides 64, 70 of tissue in an open wound 60 is shown in FIGS. 19 and 20. In this embodiment, the surgeon inserts a first curved or straight end 46 of the suture 40, such as a needle, into the tissue at a point 62 on a first side 64 of the wound 60 and laterally spaced from the face 66 of the wound 60 at the first side 64. The surgeon advances the needle 46 through the tissue along a curvilinear path until the needle 46 emerges from the tissue on a second side 70 of the wound at an exit point 72 laterally spaced from the face 68 of the second side 70 of the wound 60 and longitudinally spaced in a first direction from the point of insertion 62. This path subcutaneously passes through both faces 66, 68 of the wound 60. The surgeon grips the needle 46 and pulls the needle 46 out of the tissue for drawing the first portion 56 of the suture 40 through the tissue until the barbs 44 of the second portion 56 engage the surface of the skin 58 at the insertion point 62 preventing further advancement of the suture 40 into the tissue. The faces 66, 68 of the wound 60 are approximated by pushing the adjacent sides 64, 70 of the tissue together along the body 42 of the suture 40 in the tissue. The length of the first portion 54 of the body 42 of the suture 40 protruding from the skin 58 is cut and discarded (FIG. 19).

The surgeon then inserts the second needle 48 into the tissue at the point of insertion 62 of the first needle 46 at the first side 64 of the wound 60. The surgeon pushes the needle 48 through the tissue along a curvilinear path which substantially mirrors the passage of the first needle 46 until the needle 48 emerges from the tissue at an exit point 110 laterally spaced from the wound and longitudinally spaced in a second direction from the point of insertion 62 such that the paths of the first and second portions 54, 56 of the suture 40 overlap. Again, the path of the second needle 48 subcutaneously passes through the faces 66, 68 of the wound 60. The surgeon grips the second needle 48 and pulls the needle 48 from the tissue for drawing the second portion 56 of the suture 40 into the tissue. The length of the second portion 56 of the suture 40 protruding from the skin 58 is cut and discarded, leaving a stitch in the tissue which resembles the Greek letter alpha (FIG. 20).

This stitch has its greatest benefit in small wound and incision closure. The alpha-shaped stitch can be placed quickly in tissue as compared with conventional loop sutures. Moreover, this stitch pattern has no blood constricting loops, leaves no stitch marks on the surface of the skin, and does not have to be removed from the patient if bio-absorbable material is used. Two or more of the alpha-shaped stitches may be used to close a larger wound.

Figure 21:
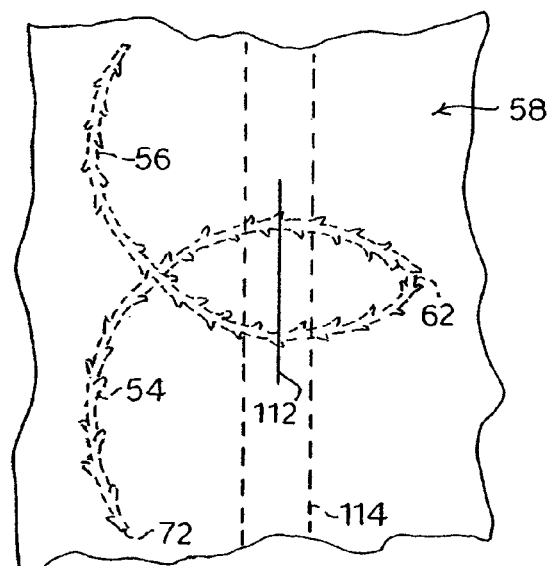
FIG. 21 is a plan view of the embodiment shown in FIGS. 19 and 20 for use in closing a vascular puncture via cinching of tissues directly above the vessel.
Figure 22:
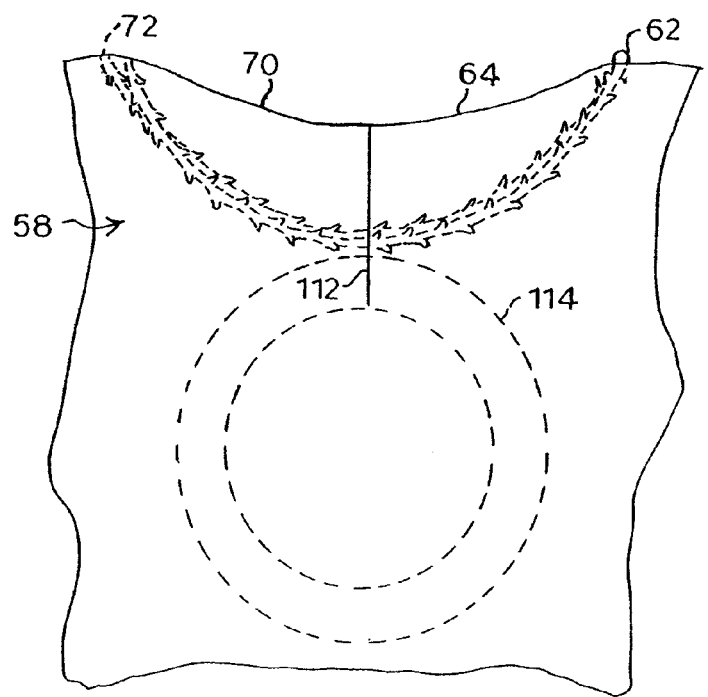
FIG. 22 is a cross-sectional view of the method shown in FIG. 21.

A particular application of the alpha-stitch according to the method of the present invention is as a means of restricting bleeding from an arterial opening by constricting the tissue above and around the arterial opening. For example, the introduction and removal of catheters into the femoral artery is typically required when performing cardiac catheterization, percutaneous interventions, and other vascular procedures. These puncture wounds are typically self-sealing after several hours of sustained external pressure at and around the insertion site of the puncture wound. FIGS. 21 and 22 show the alpha-stitch according to a method of the present invention positioned for performing this function. Note that the path of the suture portions 54, 56 is curvilinear with the respect to the skin 58 surface and that the deepest points of the arcs pass immediately above the puncture site 112 in the artery 114. In this embodiment, the ends 46, 48 of the suture 40 are pulled to put tension in the tissue. As the ends 46, 48 of the suture 40 are pulled, the tissue embraced by the suture is pulled both inward from the areas lateral to the artery 114 and downward from areas immediately above the artery 114. This constriction of tissue increases the density of tissue around the arterial puncture site 112 and imparts forces with vectors directed toward the arteriotomy site to limit bleeding. Further, this suture method avoids the need to traverse the artery wall or lumen, thus eliminating the risk of vessel wall dissection and promoting introgenic thrombogenesis.

The method of the present invention is also useful in binding together partially or completely severed tendons or other internal tissue repairs requiring considerable tensile strength. For example, referring to FIG. 23, a finger 120 is shown with a portion of the outer layer of tissue cut-away to schematically show a severed tendon 122. A Kessler suturing method for joining the two ends 124, 126 of the tendon 122 is shown in FIG. 24. This method requires the surgeon to apply an intricate stitch pattern and to complete the tendon connection with one or two technically challenging knots 128. No portion of the suture knot 128 may protrude from the outside surface of the repaired tendon 122 where it could snag the surrounding tendon sheath and impede healing. The knot 128 also presents a particular dilemma since it must be tied between the two ends 124, 126 of the tendon 122, where it can be a barrier between tendon sections that must appose in order to effectively heal. A further limitation of the conventional tendon repair method is that relatively small amounts of tension can stretch the tendon 122, allowing it to slide along the smooth monofilament fiber and effectively disrupt, or in the case of greater amounts of tension, separate completely at the wound margin. This outcome substantially limits healing even though the suture material remains intact.

Figure 25:
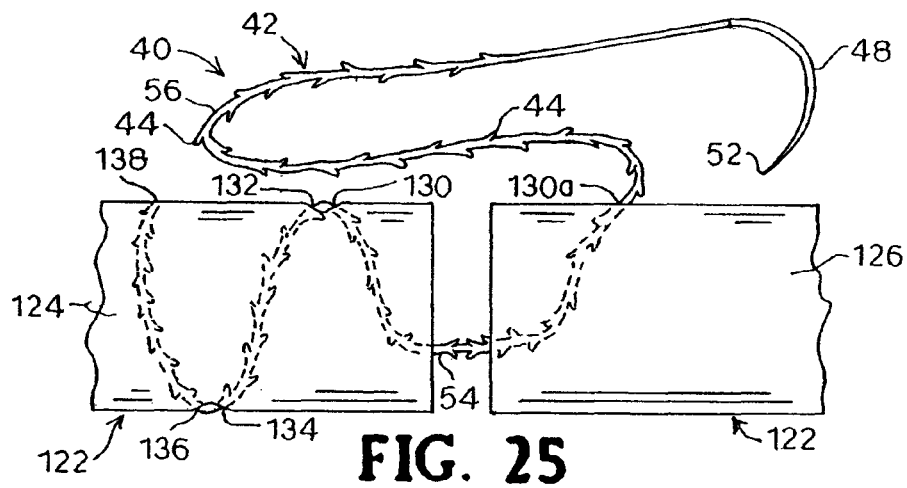

A method according to the present invention for joining the two ends 124, 126 of the tendon 122 is shown in FIGS. 25-28. Referring to FIG. 25, the surgeon begins by inserting the first end 46 of the suture 40, which may a straight or curved surgical needle, into one end 124 of the tendon 122 and pushing the needle 46 through the tendon 122 along a selected curvilinear path until the point 50 of the needle 46 extends from an exit point 130 in the periphery of the tendon 122 longitudinally spaced from the one end of the tendon 122. The first needle 46 is gripped and pulled out of the tendon for drawing the first portion 54 of the suture 40 through the tendon 122 leaving a length of the first portion 54 of the suture in the tendon end 124 between the end of the tendon 122 and the exit point 130. The surgeon reinserts the needle 46 into the periphery of the tendon 122 at an entry point 132 immediately adjacent the exit point 130 and pushes the needle 46 along a selected curvilinear path until the point 50 of the needle 46 exits the other side of the tendon at an exit point 134 that is longitudinally spaced from the entry point 132. It is understood that the surgeon could use the exit point 130 as the next entry point for the needle 46 if desired. The surgeon pulls the needle 46 out of the tendon for drawing the first portion 54 of the suture 40 through the tendon 122, reinserts the needle 46 into the side of the tendon 122 at an entry point 136 immediately adjacent the exit point 134 and pushes the needle 46 along a selected curvilinear path back out of the other side of the tendon 122 at an exit point 138 longitudinally spaced from the previous entry point 136. It is understood that the surgeon makes as many passes as deemed necessary for holding the end 124 of the tendon 122, or as the length or thickness of the tendon 122 allows, and removes the remaining length of the first portion 54 of the suture 40.

Figure 26:
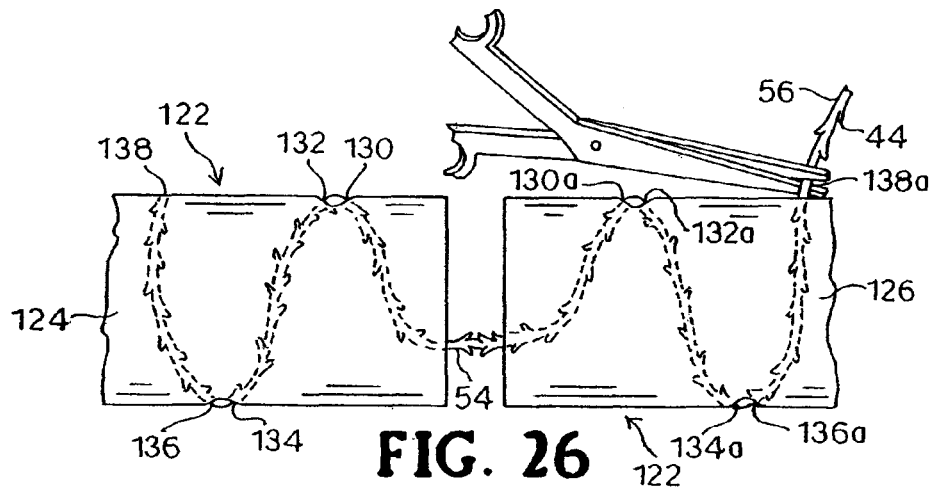

As seen in FIG. 26, these steps are repeated with the second portion 56 of the suture 40 at the other end 126 of the tendon 122. The pattern of the second portion 56 of the suture 40 in the second end 126 of the tendon 122 generally mirrors the first portion 54 of the suture 40 in the first end 124 of the tendon 122, including exit points 130a, 134a, 138a and entry points 132a, 136a. The ends 124, 126 of the tendon 122 are brought together while maintaining tension on the free ends of the sutures.

Figure 27:
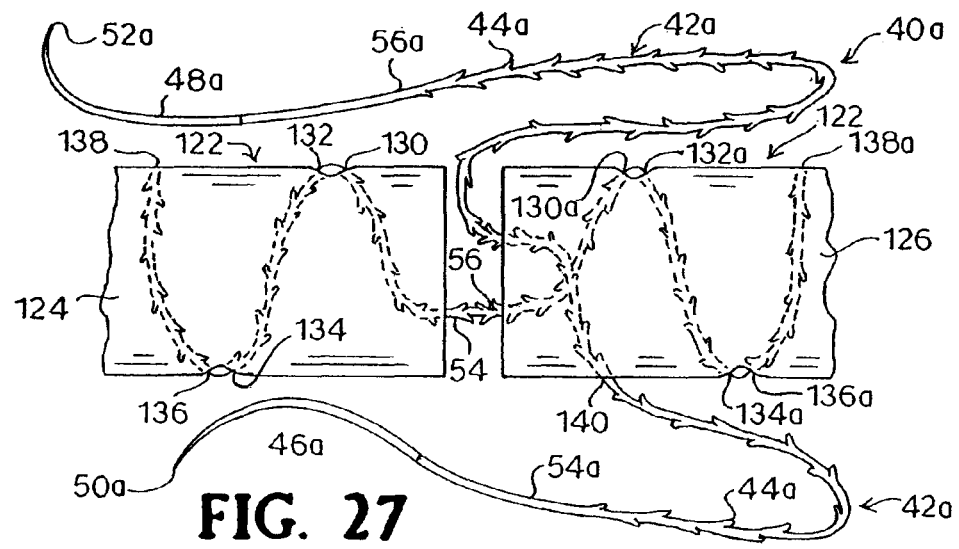

Referring now to FIG. 27, a second suture 40a is introduced at the second end 126 of the tendon 122. The first needle 46a of the second suture 40a is inserted into the end 126 of the tendon 122 and pushed through the tendon 122 along a selected curvilinear path until the needle 46a extends from an exit point 140 in the periphery of the tendon 122 substantially opposite the first exit point 130a of the second portion 56 of the first suture 40. The needle 46a of the second suture 40a is pulled out of the tendon 122 for drawing the first portion 54a of the second suture 40a through the tendon 122 leaving a length of the suture 40a in the tendon 122 between the end 126 of the tendon 122 and the exit point 140. The surgeon repeats the steps described above by reinserting the needle 46a into the tendon 122 at an entry point 142 (FIG. 28) adjacent the exit point 140 and pushing the needle 46a along a selected curvilinear path until the needle 46a emerges from an exit point 144 in the periphery of the tendon 122 substantially opposite the second exit point 134a of the second portion 56 of the first suture 40. In this manner, the surgeon advances longitudinally along the end 126 of the tendon 122 entering at 146 and exiting at 148. The previous steps are repeated at the other end 124 of the tendon 122 with the second portion 56a of the second suture 40a. The number of sutures used depends on the size, caliber, and length of the tendon to be repaired. Big tendons will require more than two sutures whereas one may suffice for very small tendons.

Tendon repair with two sutures according to the present invention exhibits equivalent or better holding power as the prior art technique. Moreover, tendons repaired according to the methods of the present invention maintain their original configuration, profile, contour, and form better when being stretched.

The method of the present invention may be embodied in many surgical procedures. The procedures include both "open" surgery as well as endoscopic and laparoscopic surgery. Further, the uses of embodiments of the present invention may include repair of wounds, fastening of tissue junctions formed by the procedures, and positioning of tissue. The surgical procedures described herein are known to those of ordinary skill in the art, and accordingly are described only to a level of detail required to convey the respective embodiments of the method of the present invention. In FIGS. 29-48, where various steps of insertion are omitted from a drawing, it should be understood that the description and accompanying text of FIGS. 1-28 apply to inserting the sutures 40.

Figure 29:
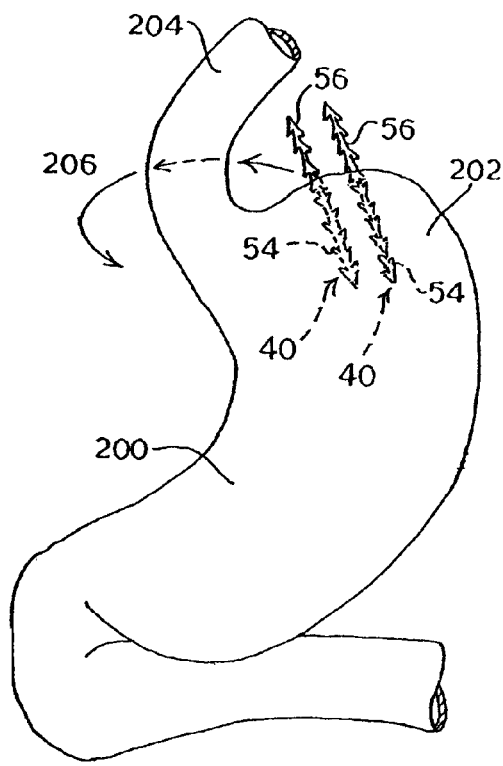
FIGS. 29-30 are side elevation views of an embodiment of the method according to the present invention for performing a Nissen fundoplication.
Figure 30:
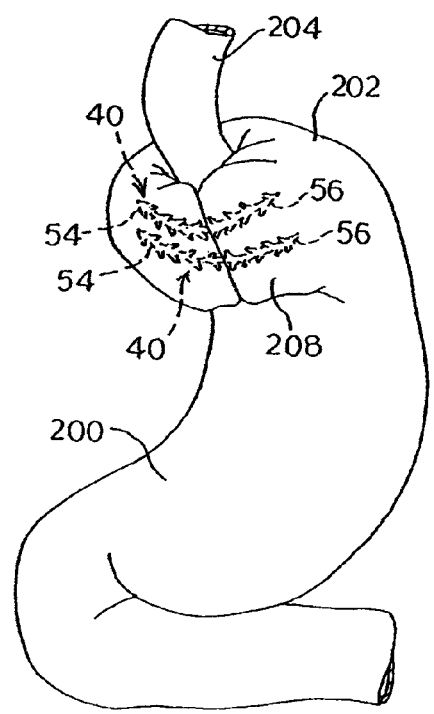

FIG. 29 shows a stomach 200 prior to performance of a Nissen fundoplication. This procedure is performed on patients who suffer from gastroesophageal reflux disease and do not respond to medical treatment. As shown, the first portions 54 of two respective barbed sutures 40 are inserted into a proximal location of the fundus 202 and into the serosal and muscularis layers, and the respective second portions 56 remain free. The stomach's fundus 202 is pulled behind and wrapped 206 around the esophagus 204. The respective second portions 56 are then advanced similarly into the apposing part 208 of the stomach 200, as shown in FIG. 30.

The same result in fastening may be achieved by performing the procedure in a different order. The fundus 202 may be pulled and wrapped 206 behind the esophagus 204 first, and then temporarily clamped or stapled in placed while the first and second portions 54, 56 are inserted in the configuration shown in FIG. 30. Other sequences may also be used and remain within the scope of the present invention.

Figure 31:
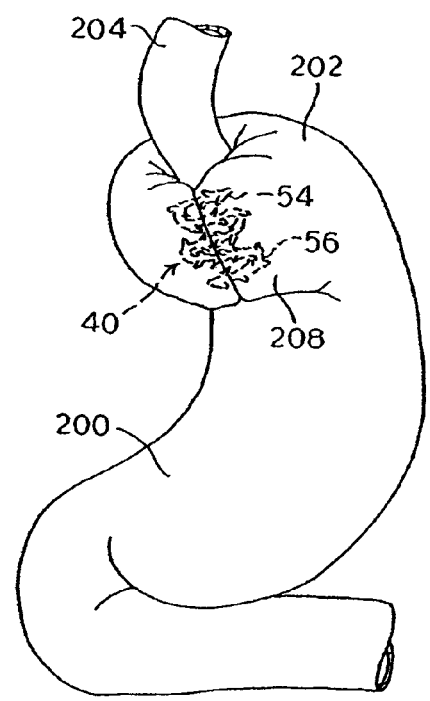
FIG. 31 is another embodiment of a method according to the present invention for performing a Nissen fundoplication.

The barbed suture 40 may also be inserted as shown in FIG. 31, in either a sinusoidal or coiled configuration as previously described. The curved insertion is performed subsequent to pulling and wrapping 206 the fundus 202 behind the esophagus 204, and then clamping or stapling in place.

Figure 32:
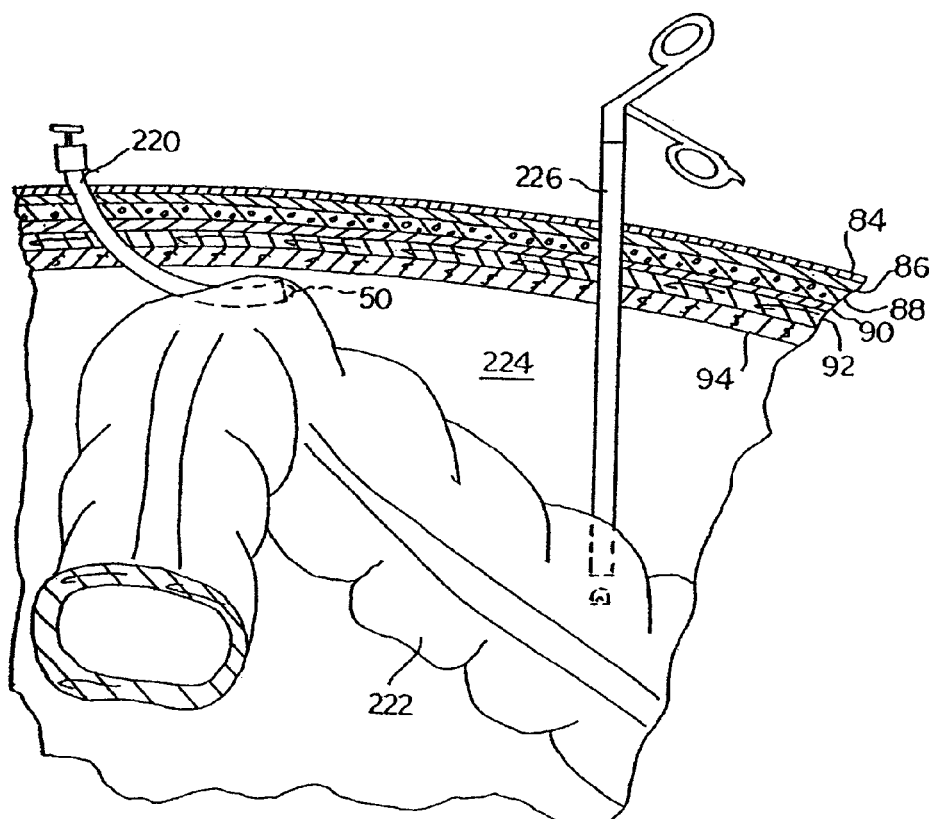
FIGS. 32-34 are cut-away perspective views of an embodiment of the method according to the present invention for laparoscopic insertion.

FIG. 32 shows a laparoscopic insertion device 220 used to stabilize a bowel structure 222 in position in advance of performing an anastomosis, whereby an end-to-end surgical connection of hollow organs is conventionally performed. The laparoscopic insertion device 220 comprises a tubular body in which the barbed suture 50 is disposed, with holes at the leading and trailing ends, similar to that disclosed in U.S. Pat. No. 5,342,376 to Ruff, the contents of which were previously incorporated by reference herein. The insertion device 220 penetrates using the point 50 of the suture to pierce the epidermis 84, dermis 86, fat 88, fascia 90, muscle 92, and the peritoneum 94 before passing into the abdominal cavity 224. The insertion device 220 then passes into the bowel structure 222. A laparoscopic grasping tool 226 is shown to be holding the bowel structure in position until the suture is in place. It should be noted that the bowel structure 222 may also be stabilized by placement of a barbed suture 40 from the inside of the structure 222.

Figure 33:
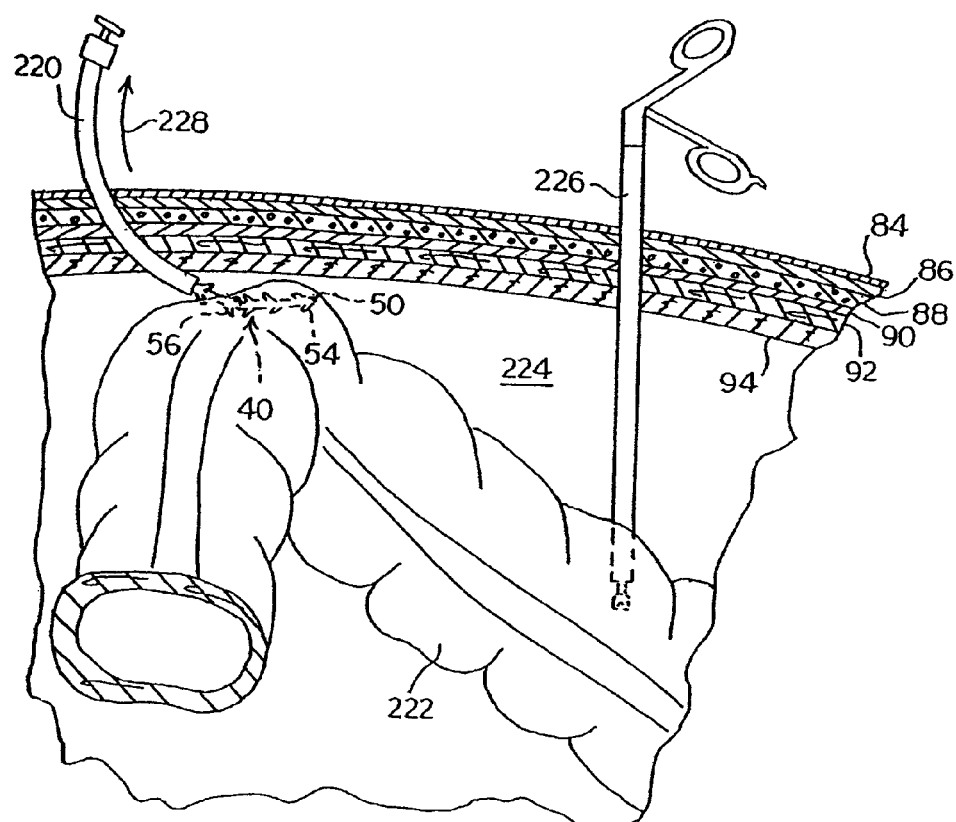

In FIG. 33, the laparoscopic insertion device is removed by pulling it outward 228, exposing the suture 40, while the pointed end 50 of the suture 40 is retained by its barbs against the removal force of the insertion device 220. The suture 40 is in place in FIG. 34. When the procedure that gave rise to the need to tie the bowel structure 222 in place is complete, the suture may be cut at an exposed point 229. As shown, the trailing end of the suture 40 extends through the epidermis 84 at the point of initial insertion, and the suture 40 may be cut at point 229 to allow that portion of the suture 40 to be removed by pulling on the trailing end.

Optionally, the barbed suture pointed end 50 may continue through the bowel structure 222 tissue, into the abdominal cavity 224, and through any number of desired selected layers of the peritoneum 94, muscle 92, fascia 90, fat 88, dermis 86, and epidermis 84. If the suture 40 passes through the epidermis 84 and is to be left in place, the suture 40 my be cut off such that the end of the suture 40 resides beneath the epidermis 84. Alternatively, in a method similar to that described for FIG. 34, when the procedure that gave rise to the need to tie the bowel structure 222 in place is complete, the suture 40 may be cut at the exposed point 229 and in addition at another exposed point along the suture 40 on the opposite side of the bowel structure 222, allowing removal of both ends of the suture 40.

Figure 35:
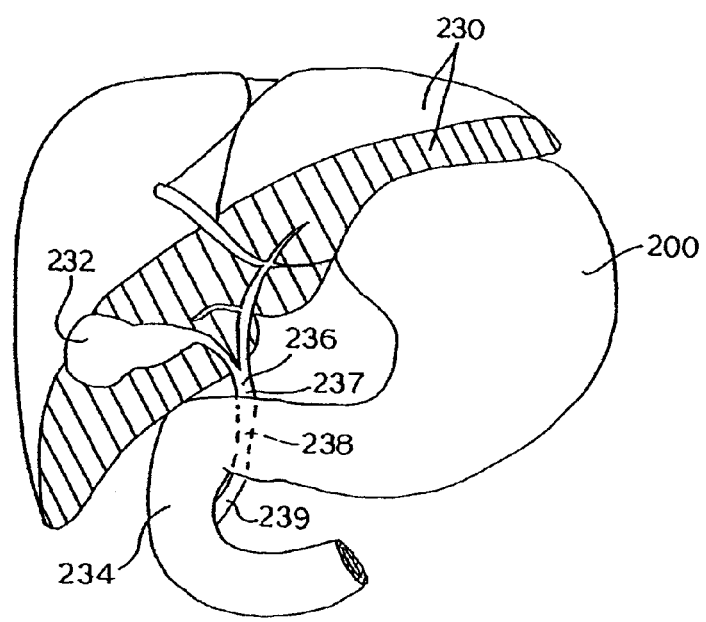
FIGS. 35-37 are perspective views of two embodiments according to a method of the present invention for performing an anastomosis of a liver bile duct to a portion of a bowel.
Figure 36:
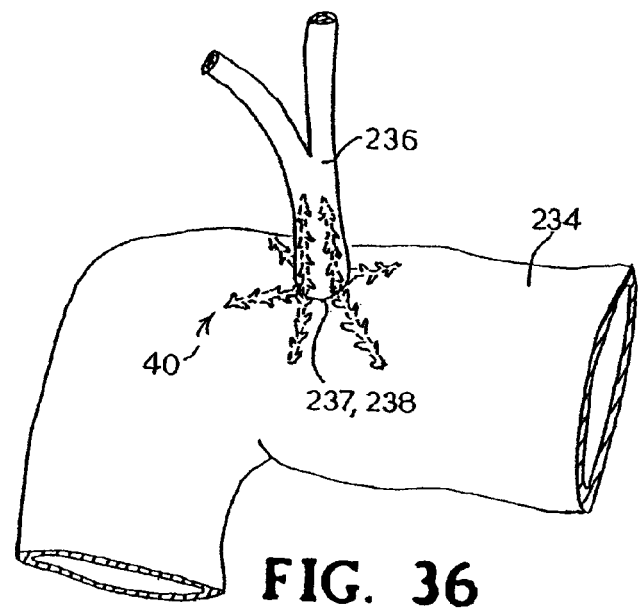
Figure 37:
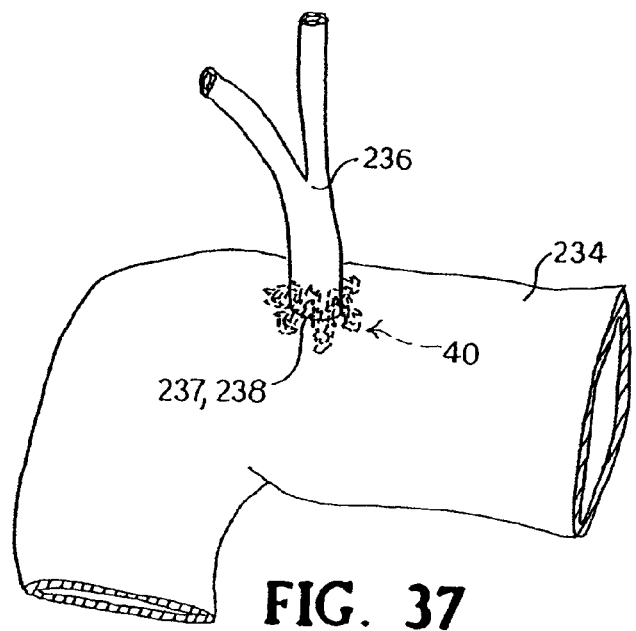

A portion of the biliary system is shown in FIG. 35. The liver 230 is shown in partial section view, and the gallbladder 232, bowel 234, and stomach 200 are the other organs that are shown. The barbed suture of the present invention may be used to perform a Rodney Smith procedure with Roux-en-Y for the anastomosis of the bowel 234 to the liver 230. In such an operation, the bile duct 236 may be cut, for example, at point 237 and anastomized to the bowel 234 at an incision in the bowel 234 at point 238. The sutures 40 may be inserted as shown in FIG. 36 with either an insertion device or with needles as previously discussed. The remaining portion of the bile duct 239 is removed and the wound at the end where it connects to the bowel 234 is sutured closed, which may also be done with sutures 40 of the present invention. In addition, barbed sutures can be placed in a curvilinear path, as shown in FIG. 37 by proceeding with the suture around the bile duct 236 and the opening in the bowel. The first insertion point of the suture may be either in the bowel or the bile duct.

Figure 38:
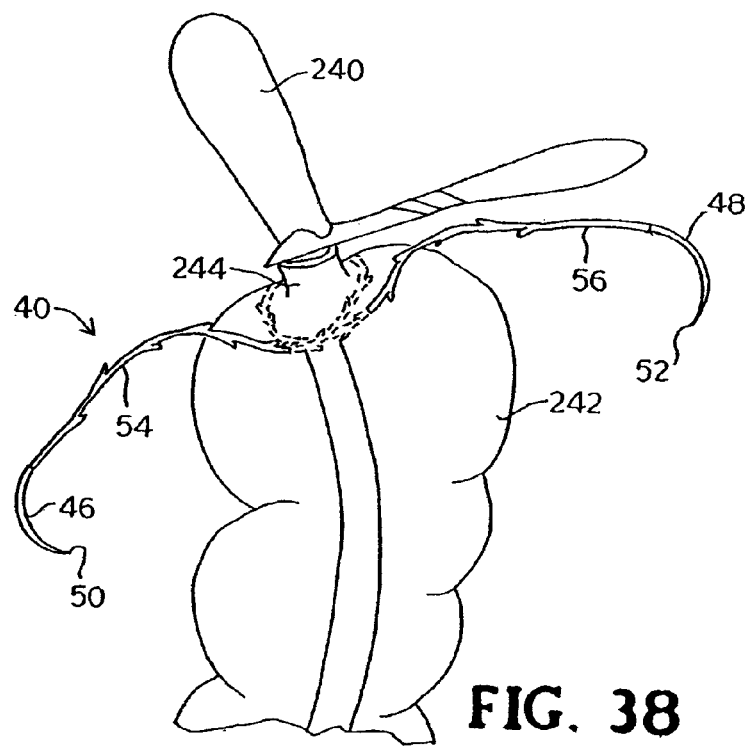
FIGS. 38-39 are perspective views of an embodiment of the method according to the present invention for performing an appendectomy.

The appendix 240 is being removed from the cecum 242 of the large intestine in FIG. 38. Prior to cutting of the appendix 240, the suture 40 must be placed so that it will be ready to tie off the appendiceal stump 244. The suture 40 may be placed using a curved insertion device (not shown), or with curved needles 46, 48. The barbed suture 40 is placed around the base of the appendix 240 by inserting the first end of the first portion of the suture at an insertion point 62 (FIG. 39) and pushing the first portion 54 in one direction through the muscularis and serosal layers of the cecum 242 around the base for at least one half of the circumference. Then the second portion 56 is likewise placed by inserting at the insertion point 62 and pushing the second portion 56 in the other direction through the muscularis and serosal layers of the cecum 242 around the base for at least until the second portion 56 crosses the first portion 54. The appendix 240 is then removed, and the stump 244 is inverted while the suture 40 is pulled taut, similar to a "purse-string" as well as the alpha stitch shown in FIGS. 19-22.

Although FIG. 38 shows both needles 50, 52 and respective suture end portions 54, 56 extending from the cecum 242, having both end portions 54, 56 extend from the cecum 242 is optional. With the use of an insertion device of the nature of that shown in FIG. 33, for example (device 220), one end may be left embedded in the cecum 242 and the other end may be pulled to invert the appendiceal stump 244 with the purse-string or alpha stitch.

Figure 40:
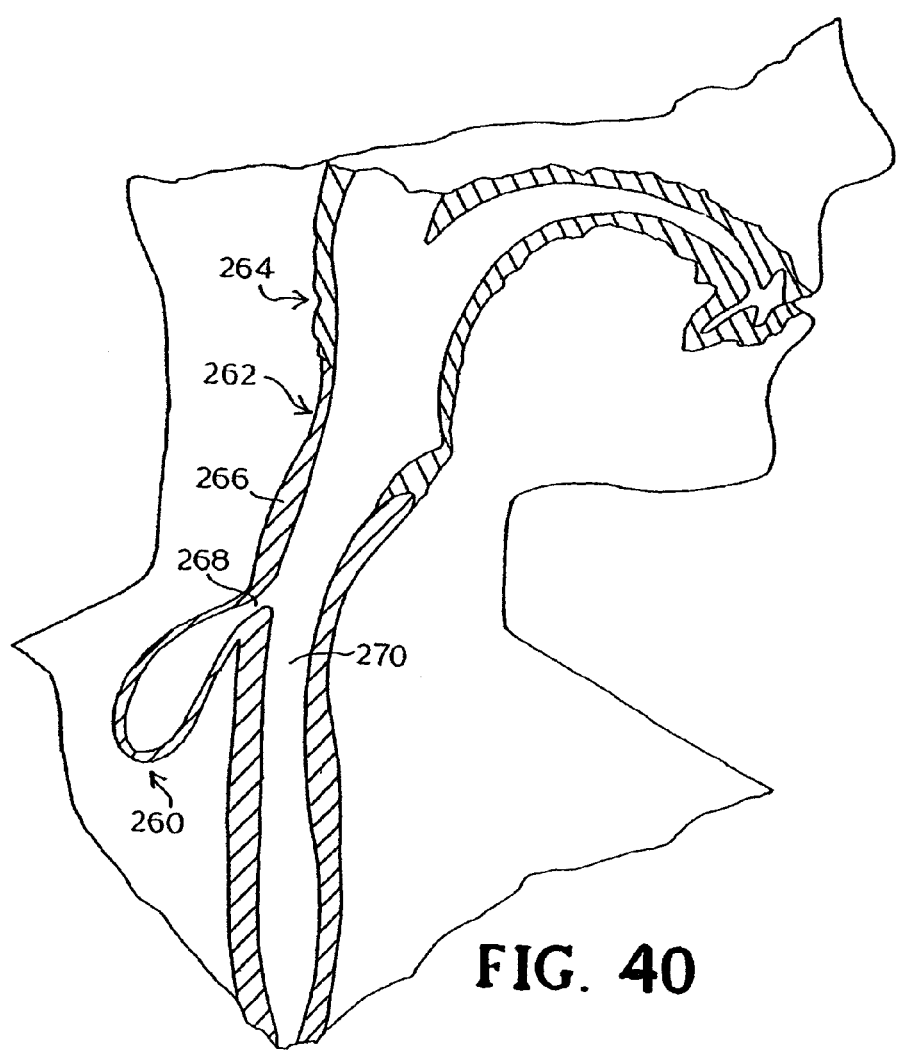
FIGS. 40-42 are vertical cross-section views of an embodiment of the method according to the present invention for performing a Zenker's Diverticulectomy.
Figure 41:
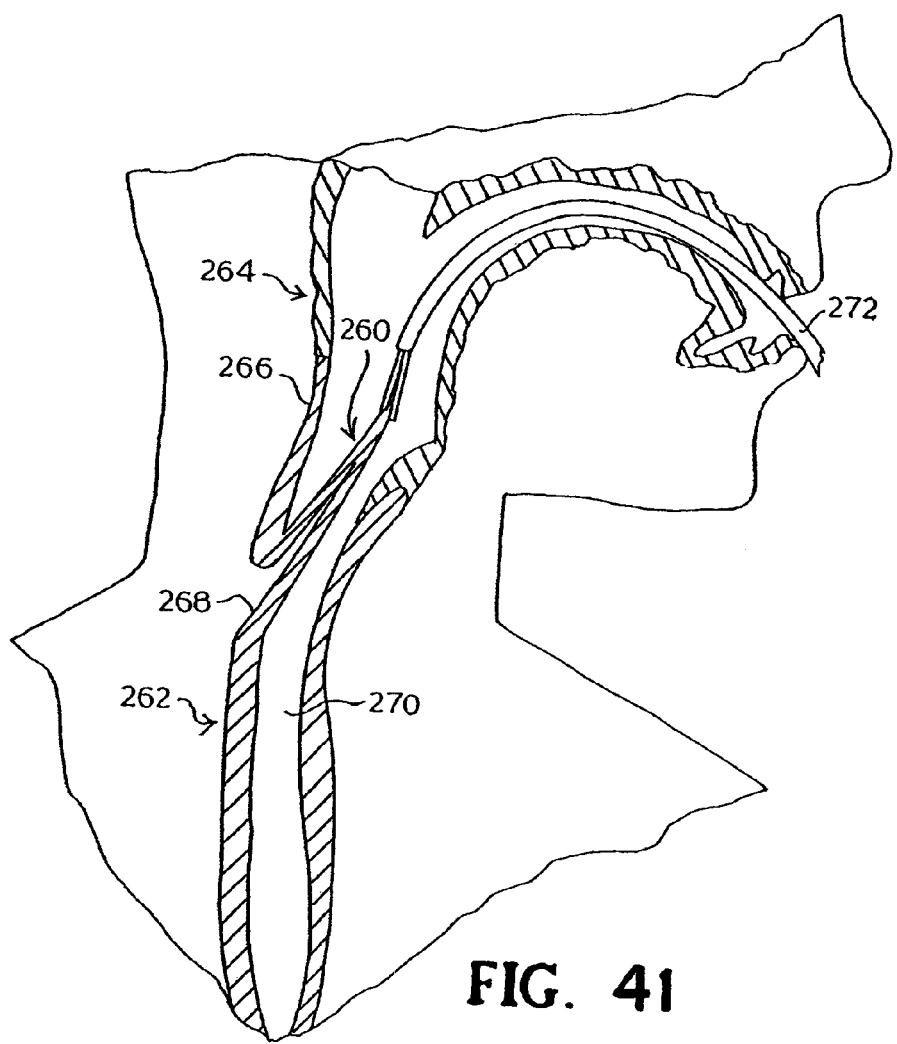
Figure 42:
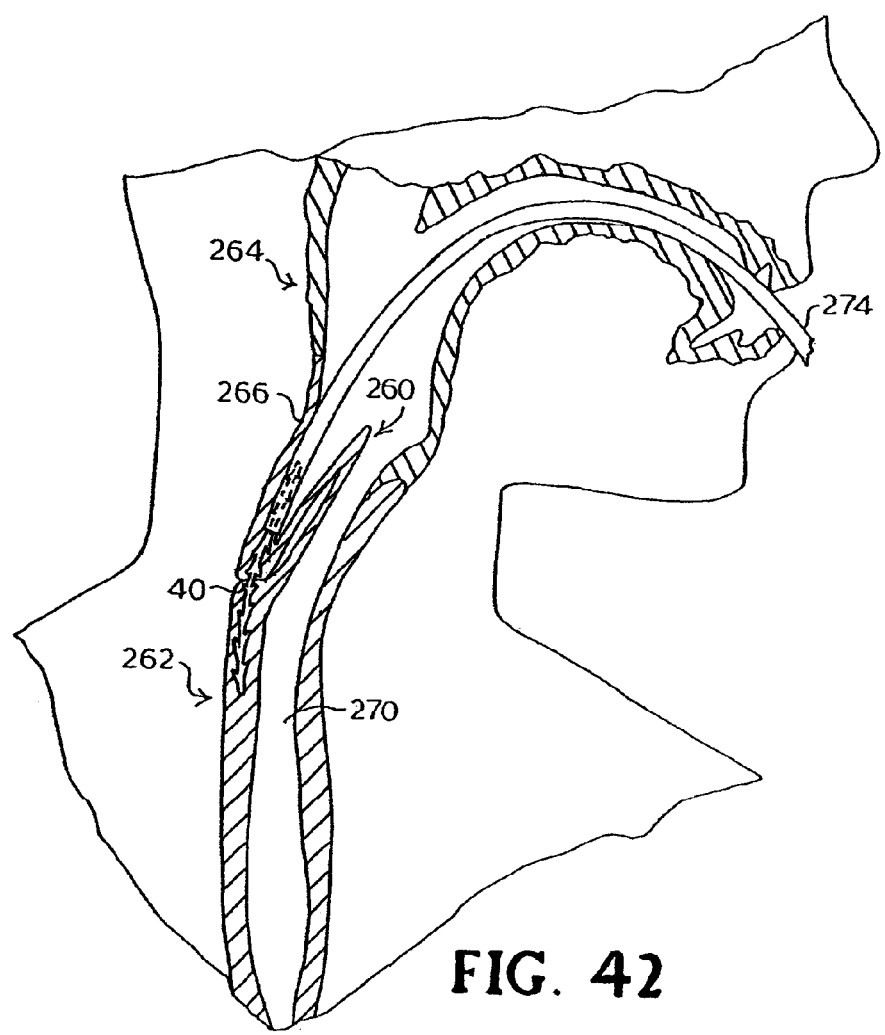

FIGS. 40-42 show three stages of the procedure for a Zenker's Diverticulectomy. A Zenker's Diverticulum 260 is a sac that protrudes from the esophagus 262 below the pharynx 264. The Diverticulum 260 is the herniation of the mucosal sac between the fibers of the pharyngeal constrictor muscle and the cricopharyngeal muscle 266. The Diverticulum forms an orifice 268 to the lumen 270 of the esophagus 262, and is shown in its initial untreated position in FIG. 40.

Figure 34:
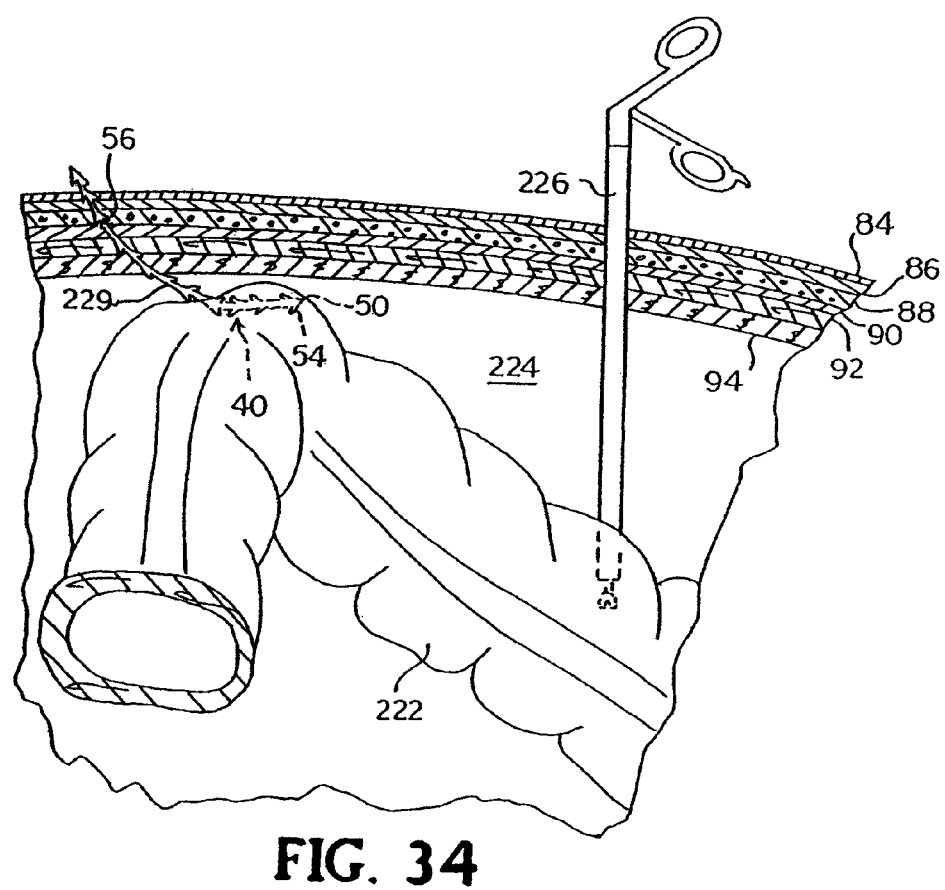
Figure 39:
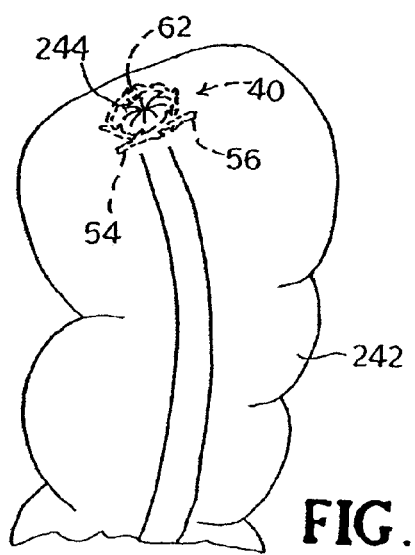

In FIG. 41 the Diverticulum 260 is inverted and pulled into the esophagus 262 through the orifice 268 using an endoscopic grasping tool 272. An endoscopic insertion device 274, similar to the laparoscopic insertion device 220 of FIGS. 32-34, is used as shown in FIG. 42 to insert the barbed suture 40 into the cricopharyngeal muscle 266 above the orifice 268, exiting at the orifice, and then again penetrating the muscle 266. The muscle 266 on both sides of the orifice 268 is approximated to close the orifice. The Diverticulum 260 is then endoscopically cut and removed (not shown). Alternatively, the stitch used to close the orifice 268 may be a purse-string type or alpha type, as shown in FIGS. 38 and 39. Multiple sutures may be used to close the orifice. Further, the procedure of suturing closed the orifice may be performed in a similar manner without inverting the Diverticulum 260 into the esophagus 262. In this alternative the Diverticulum remains outside the esophagus 262 and is not excised.

Figure 43:
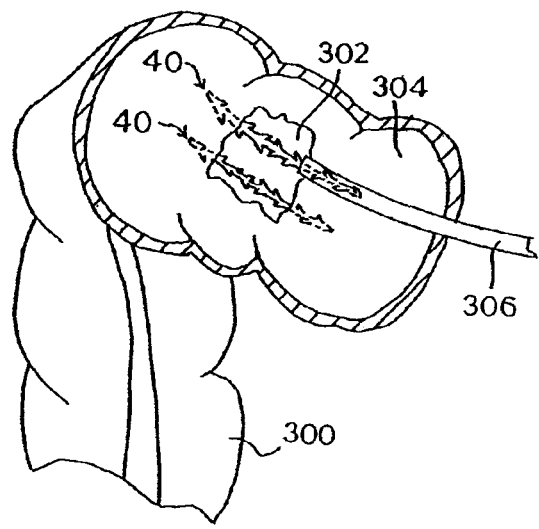
FIGS. 43-44 are partially sectioned perspective views of an embodiment of the method according to the present invention for closure of ulcerative intestinal lesions or other bowel wall defects.
Figure 44:
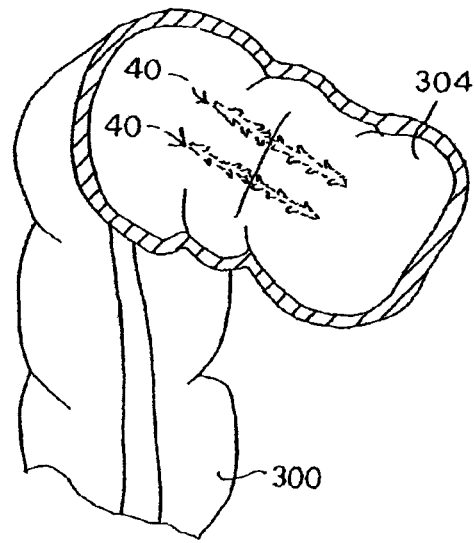

The viscus structure 300 shown in FIGS. 43-44 has an ulcerative lesion 302 on its inside wall 304. An endoscopic camera 306 ("scope") allows the procedure to be performed, and an endoscopic insertion device (not shown) in a separate tube within the scope inserts the sutures 40 as previously described. The scope 306 may approach the lesion 302 through the anus or the oropharynx. The tissue on each side of the lesion 302 is approximated and the endoscopic devices are removed as shown in FIG. 44.

Figure 45:
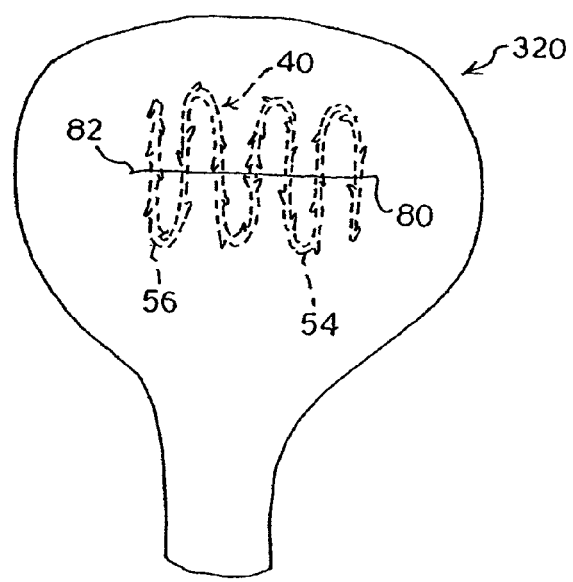
FIG. 45-46 are front elevation views of two embodiments of the method according to the present invention for closure of a cystostomy incision in the urinary bladder.
Figure 46:
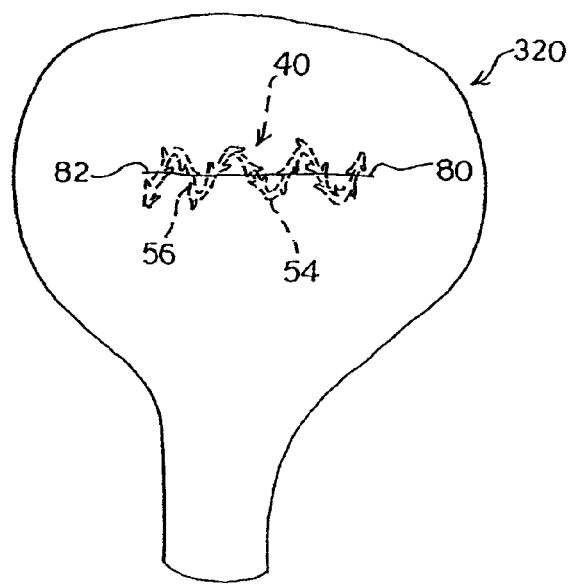

FIGS. 45 and 46 respectively show a closure of a cystostomy incision in a urinary bladder 320. The closure is shown as having a curvilinear path, and may be inserted in such a curvilinear path similarly to the sinusoidal method (FIG. 45) or coil method (FIG. 46) previously discussed and shown by FIGS. 7-10 and FIGS. 12-15, respectively, although other methods discussed herein may also be used. The suture 40 passes through the muscularis layer of the bladder in a bidirectional fashion.

Figure 47:
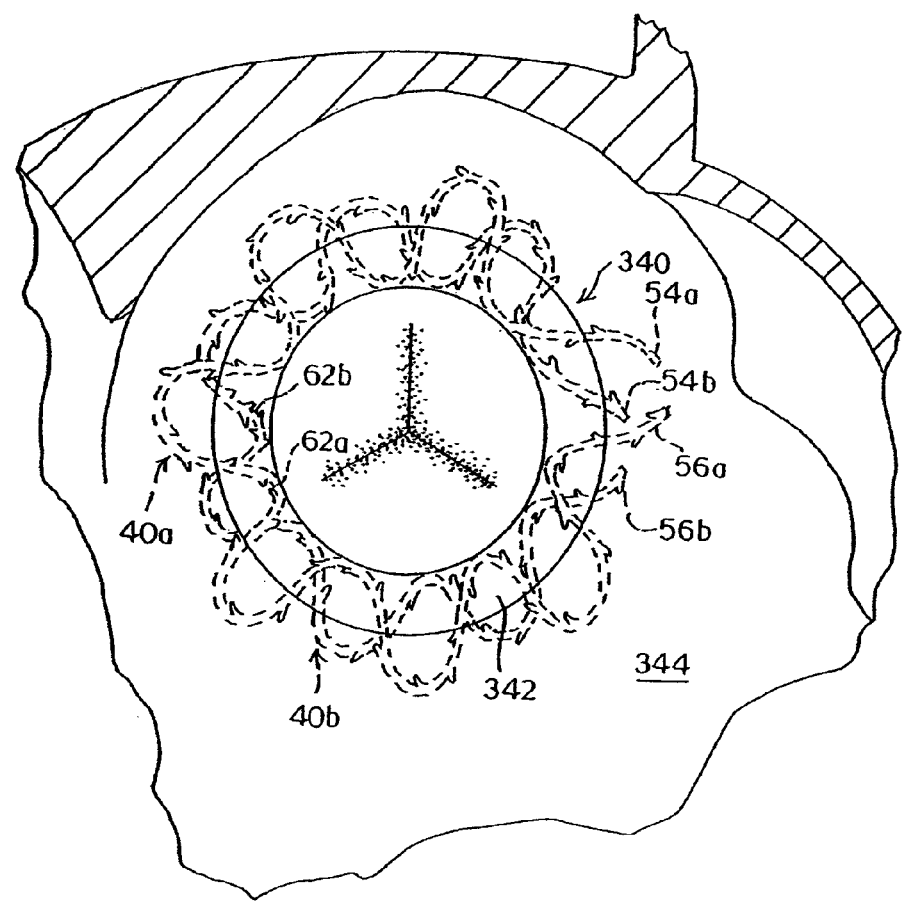
FIG. 47 is a front elevation view of an embodiment of the method according to the present invention for securing prosthetic heart valves.

A replacement heart valve 340 is shown in FIG. 47. The annular cuff 342 of the heart valve 340 forms the periphery of the valve. The cuff 342 is joined to fibrous heart tissue 344 that forms a ring in the location where the valve 340 is placed. Two sutures 40a, 40b are shown, respectively having first portions 54a and 54b that pass through the cuff 342 and tissue 344 in one direction and second portions 56a and 56b that proceed in the other direction. Threading of the sutures 40a, 40b is performed similarly to the sinusoidal and coil methods previously discussed, and may start from either the cuff 342 or the tissue 344.

Various configurations may be used to install the valve 340 in accordance with the knowledge of one of ordinary skill in the art, such as only one suture for the full periphery of the valve, or multiple sutures that each include a portion of the valve's periphery, and providing redundancy of sutures as appropriate. The replacement heart valve may be a bioprosthetic valve or an artificial prosthetic mechanical valve. In addition, this method may be used on any foreign element that has a periphery and requires attachment to tissue, for example, a patch for closing a septal defect in the heart.

Figure 48:
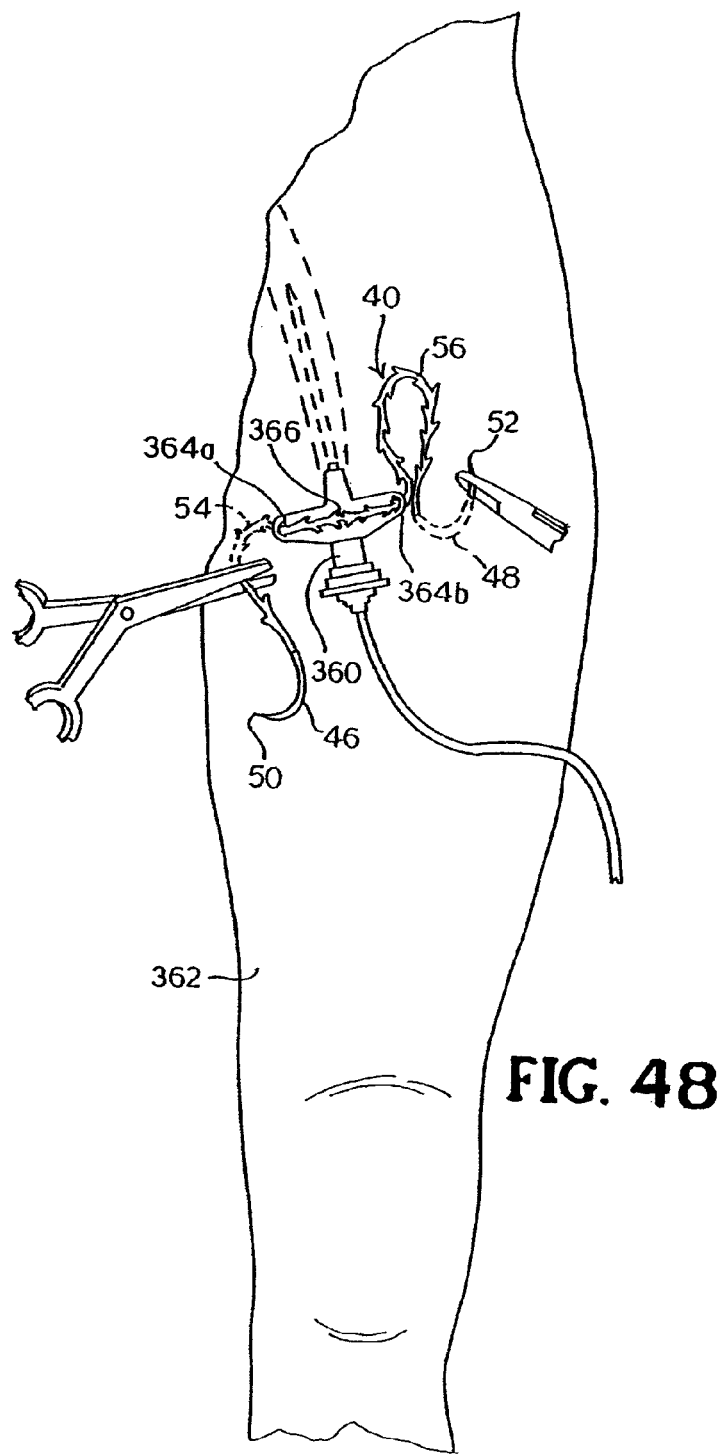
FIG. 48 is a front elevation view of an embodiment of the method according to the present invention for securing a catheter in position.

The method according to the present invention may also be used to secure devices to tissue, both inside and outside of a body. A central line device 360, as used for intravenous access, is shown in FIG. 48, and is attached to a person's leg 362. Examples of other devices that are required to be secured include catheters and monitors; tumor monitors in particular are an example of an internal device that may benefit from the method of the present invention. Eyelets 364a, 364b are provided on the device 360 and the suture 40 passes through each eyelet 364a, 364b before penetrating and passing through tissue of the leg 362 in a manner similar to that previously described, and being pulled snug to secure the device 360.

To facilitate removal of the barbed suture 40, the suture 40 may be cut at a point within the central portion 366, separating the portions of the suture 40 with opposing barbs. Then the separate sections 54, 56 of the suture 40 may be removed by pulling on an exposed portion in the direction that the barbs allow movement of the suture 40 through the tissue. This method of removal is not limited to the use shown in FIG. 48, but may apply to any use of the barbed suture.

The barbed sutures of the present invention may also be used in a variety of cosmetic surgery applications. Such applications include but are not limited to facelifts, browlifts, breast lifts, and thigh lifts. In each of the procedures, once the sutures are in place and as tension is maintained on the free ends of the suture (not shown in the figures referenced below), the engaged tissues are manually grouped and advanced toward the insertion point to achieve the desired lifting effect.

The tissue into which the sutures are inserted are soft tissue, meaning any tissue that is not an organ or a vessel. Multiple sutures may be used for further augmentation or maintenance of lift.

Figure 49:
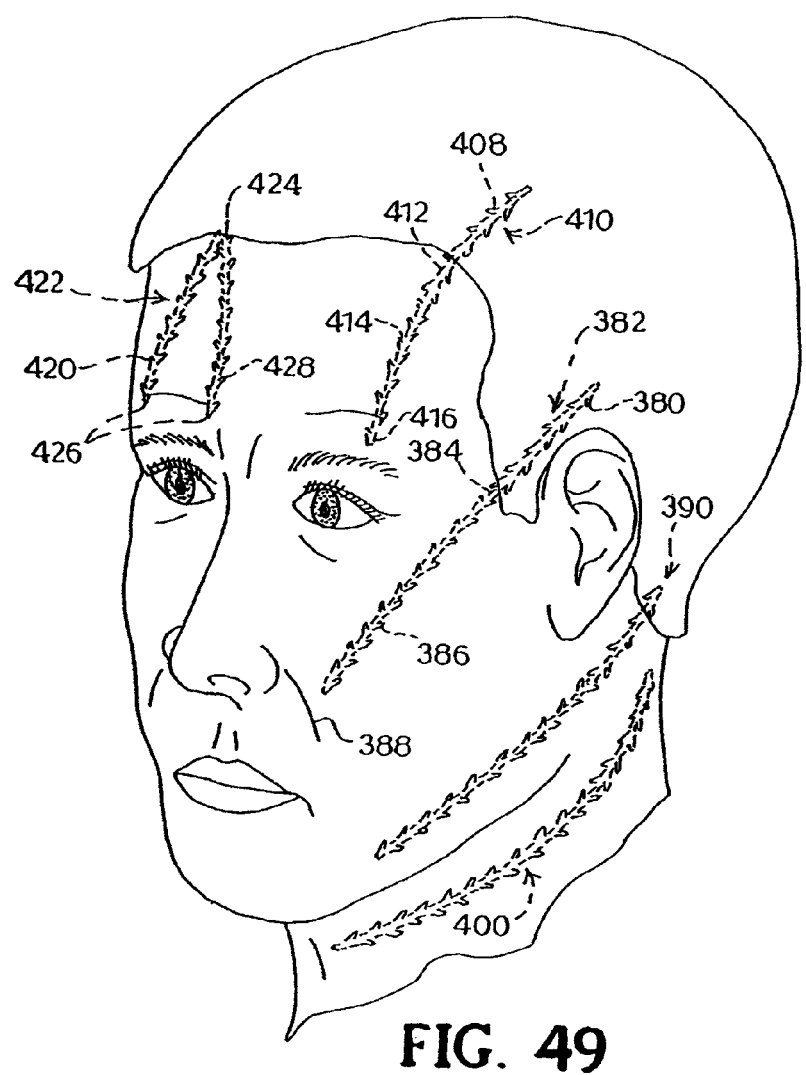
FIG. 49 is a perspective view of embodiments of the method according to the present invention for performing cosmetic surgery.

A facelift and two methods of browlifts are shown in FIG. 49. One end 380 of a barbed suture 382 is inserted using a needle (not shown) at the temporal hairline at point 384 and advanced through the subepidermal tissue underneath the scalp, exiting distally. Subepidermal tissue comprises the papillary dermis, reticular dermis, subcutaneous tissue, or any combination thereof. The other end 386 is inserted at the same location and extended towards the nasolabial fold 388, engaging the subepidermal tissue, the superficial muscular aponeurotic system, or both, and exiting distally. As tension is maintained on the free ends (not shown) of the suture 382, the engaged tissues on the lower end 386 are manually grouped and advanced toward the insertion point 384 to achieve the desired lifting effect. The procedure is repeated on the opposite side of the face. Similar procedures may be performed to provide the lifts made in other locations with barbed sutures 390, 400.

In addition, the barbed sutures may be applied with the use of an insertion device as previously discussed. For example, the barbed sutures 382, 390 shown in FIG. 49 may be put in place using an insertion device from either end of the respective suture.

One method of performing a browlift is shown with one end 408 of a barbed suture 410 being inserted at point 412 at the hairline (for nonreceding hairlines, as depicted) or at the midpoint between the hairline and the eyebrow (for receding hairlines, not shown). This end 408 is advanced through the subepidermal tissue towards and on through the scalp. The other end 414 is inserted at the same point and advanced through the subepidermal tissue in the opposite direction, exiting at the inferior aspect 416 of the brow. The procedure is repeated on the opposite side of the forehead, but for convenience herein a different method is shown in the same figure. Once again, the suture 410 may be put in place with the use of an insertion device from either end.

A second method of performing a browlift is shown in FIG. 49 with one end 420 of a barbed suture 422 being inserted at point 424 at the hairline (for nonreceding hairlines, as depicted) or between the hairline and the eyebrow (for receding hairlines, not shown). This end 420 is advanced through the subepidermal tissue, exiting at the inferior aspect 426 of the brow. The other end 428 is inserted at the same point and is also advanced through the subepidermal tissue, but at a slight angle to the path taken by the first end 420 and also exiting at the inferior aspect 426 of the brow. This results in the approximate inverted vee-shaped configuration shown. The procedure may be repeated across the forehead.

Barbed sutures of the present invention may similarly be used as a tissue-sculpting device to perform a thigh or breast lifting procedure. These procedures are similar to those shown for the facelift and browlift of FIG. 49, and accordingly no additional drawings are required but respective descriptions are as follows.

To perform a thigh lift, multiple sutures are inserted by needle at the inguinal crease, spaced approximately 0.5-1.5 cm apart, beginning at the lateral aspect of the pubic triangle and extending medially approximately 180 degrees to the vicinity of the gluteal fold. The suture is advanced approximately 8 cm cranially through the subepidermal tissue. The opposite end of the suture is inserted in the same location and similarly advanced approximately 8 cm caudally. After exiting through the skin distally at each end, tension is maintained on the free ends of the suture, and the engaged tissues are manually grouped and advanced toward the insertion point to achieve the desired lifting effect. The process is repeated with multiple sutures around the semi-circumference of the thigh, and then repeated on the opposite thigh.

To perform a breast lift using a barbed suture of the present invention, one end of the barbed suture is inserted by needle into the skin at the upper aspect of the breast curvature. The needle is advanced such that the medial barbs engage the subcutaneous and dermal tissues, while the distal barbs engage the pectoralis muscle (and where possible, the periosteum of the clavicle), and then exit distally through the skin. The other end of the suture is inserted at the same point by needle, and advanced caudally through the fibrous and fatty tissues of the breast exiting at various points along the lower curvature of the breast. Additional sutures are similarly inserted at a variety of appropriately spaced locations along the breast. As tension is maintained on the free suture ends, the breast is lifted along the axis of the suture, with the barbs locking the lift into place. Lifting is continued until the desired effect is achieved. Results from such a procedure may benefit from the use of a barbed suture with longer barbs than may be necessary in other procedures, in order to grasp fatty breast tissue effectively.

Figure 50:
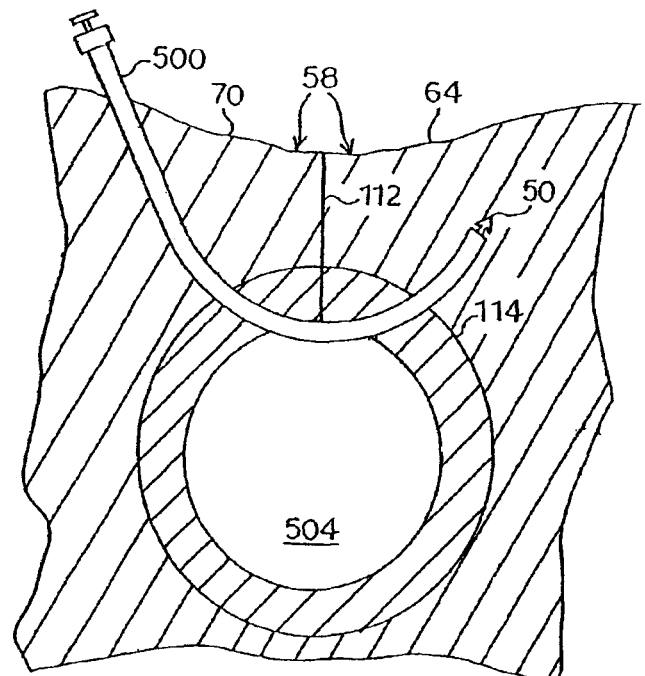
FIGS. 50-52 are cross-section views of an axial wound closure in a blood vessel according to two embodiments of the present invention.

In FIG. 50, an insertion device 500 is shown in a procedure to close an axial wound in a blood vessel, such as an artery or vein. The wound 112 is similar to that shown in FIG. 22, but the method is different in that the method of FIG. 22 uses needles and does not penetrate the artery 114, rather constricting the tissue above and around the arterial opening. The insertion device 500 of FIG. 50 comprises a tubular body in which the barbed suture 50 is disposed. The wound 112 may be a puncture in an artery 114 as occurs as the result of the introduction and removal of catheters, as discussed in the text accompanying FIG. 22. The sharp pointed end 50 of the suture 40 is pushed with the leading end of the insertion device 500 through the skin 58 and tissue 70 on one side of the artery 114, through the artery wall on one side of the wound 112, into the interior 504 of the blood vessel 114, through the artery wall on the other side of the wound 112, and into the tissue 64 on the other side of the wound 112. The trailing end of the insertion device 500 is then pulled on to remove the insertion device 500, leaving the suture 40 in place.

Figure 51:
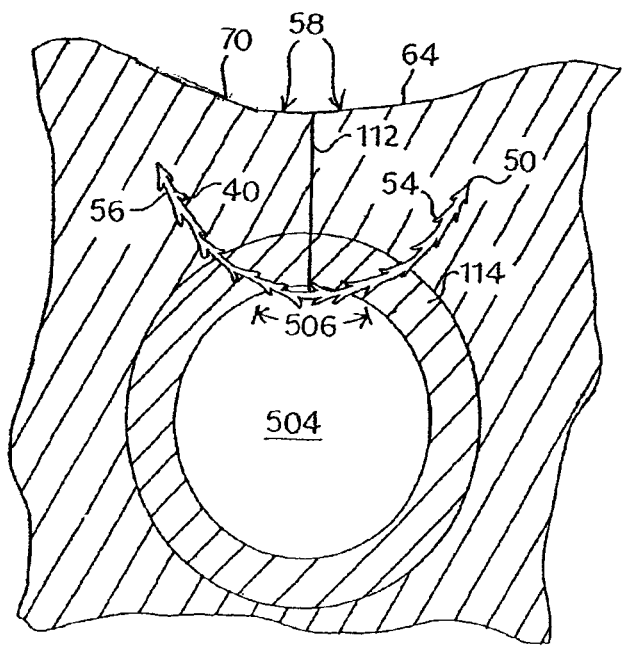
Figure 52:
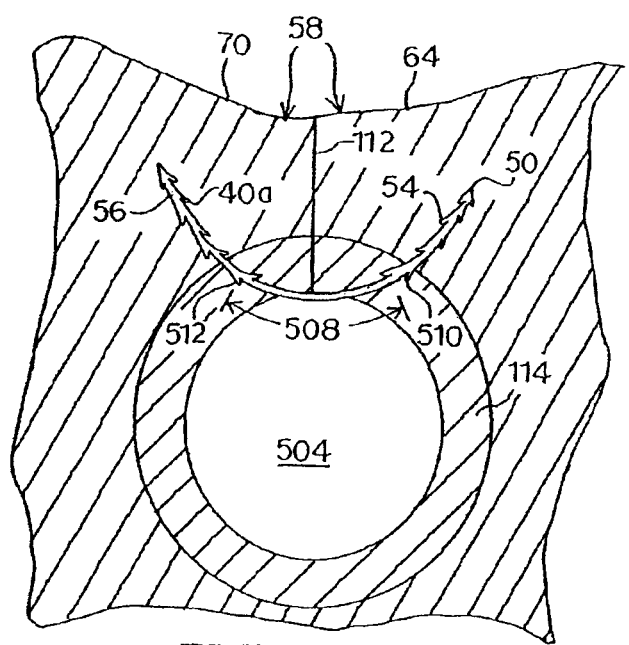

Two embodiments of a suture left in place by an insertion device are shown in FIGS. 51 and 52. In FIG. 51, the portion 506 of the suture 40 in the interior 504 of the artery 114 has barbs. The embodiment of FIG. 52 omits barbs in the interior 504 of the artery 114, and the barbs are omitted for a portion 508 that extends into the artery 114 wall. The portion 508 without barbs could extend less or more than shown, and into the tissue 70, 64, so long as there are no barbs inside the artery 114. To reduce the chance of clotting of blood on or around the suture, an antithrombotic agent may be applied on the suture. Although FIGS. 50-51 show the suture 40 with the pointed end 50 embedded in tissue 70, 64, the suture 40 may also be put into place with the pointed end 50, or both ends, extending out of the skin 58, where the end or ends may be cut.

The invention is further illustrated by the following non-limiting examples.

EXAMPLE 1

A straight incision wound, about 1.5 cm deep, was created in each of four samples of cadaveric porcine skin tissue. The tissue samples measured 4 cm by 10 cm. Each incision was centered on the skin sample so that the wound was 4 cm long from end to end.

Each wound was closed according to a different suture method using identical barbed sutures made from monofilament PDS (polydioxanone) size 0. One wound was closed according to the method shown in U.S. Pat. Nos. 5,342,376 and 6,241,747, without using the inserting device ("the Ruff method"). Seven sutures were placed along the length of the wound and running generally perpendicularly to the faces of the wound. When placed, the sutures dipped below the incision line thus engaging subcutaneous tissue below the incision and the ends of the sutures engaged some dermis. A second wound was closed using seven needle-tipped sutures placed along the length of the wound in the dermis and running generally perpendicularly to the faces of the wound similar to the method shown in U.S. Pat. No. 5,931,855 ("the Buncke method"). In both methods, the length of each suture buried under the skin was approximately 6 cm. A third wound was closed using the "zigzag" stitch pattern in the dermis as described above and shown in FIGS. 3-6. The number of passes resulted in four entry/exit points on each side of the wound. A fourth wound was closed using the corkscrew-shaped stitch pattern described above and shown in FIGS. 12-15. The number of passes resulted in seven complete loops with the tops of the loops engaged in the dermis. The tissues were held together only by the sutures.

Biomechanical strength testing was carried out as follows. Each sample was positioned so that the surface of the tissue sample was substantially vertical and the incision was generally horizontal. The bottom edge of the sample was immovably secured. The upper edge of the sample was attached to a Berkley digital fish scale (0-50 lb.) The scale was then raised vertically generating tension across the wound. The scale was raised until the tissues totally separated. The peak force required to separate the incision was recorded as the breaking strength.

TABLE 1

| Suture Method | Breaking Strength (lbs.) |
| --- | --- |
| Ruff Method | 4.5 |
| Buncke Method | 8.5 |
| Zigzag Method | 18.3 |
| Corkscrew Method | 16.5 |

EXAMPLE 2

Seven incisions were made at various locations on each of three dogs. The length of the incisions ranged from ½ inch to 4 inches and the depth of the incisions from the dermis to the muscular level. The incisions were closed with barbed sutures made from monofilament PDS (polydioxanone) size 0 and conventional sutures according to the following scheme with the locations randomized:

TABLE 2

| Tissue Level | Barbed Suture Method | Conventional Suture Method |
| --- | --- | --- |
| Dermis | Alpha, Zigzag | Simple interrupted loop stitches [2-0 nylon, 2-0 silk] |
| Subcuticular | Corkscrew | Simple continuous loop stitches [3-0 PDS] |
| Subcutaneous | Corkscrew | Simple continuous loop stitches [3-0 PDS] |
| Muscular | Corkscrew | Simple continuous loop stitches [3-0 PDS] |

More than one alpha-shaped stitch was used for longer incisions.

The dogs were housed for two weeks. Daily clinical and necropsy observations were performed on all surgical sites. With the exception that three of six sites closed by nylon sutures had some sutures chewed out by the dog, all incisions healed normally and no dehiscence occurred. The other three sites closed with nylon sutures had a "railroad-tile" appearance, one site in particular being very pronounced. None of the topical skin sites closed with barbed sutures had such an appearance. This example shows the efficacy of barbed sutures in an in vivo model.

The methods of the present invention have a number of advantages, including improving the biomechanical performance of barbed sutures. The curvilinear placement paths of the suture, as contrasted with linear insertion, provide substantially increased strength for holding the edges of a wound together. Moreover, the insertion of a single suture with curvilinear techniques replaces the insertion of a plurality of sutures. The new methods provide an efficient means for a surgeon to close a wound, reducing the time necessary to place the suture and the trauma to the patient. Surgeons can quickly and easily utilize the suturing methods during any type of surgery to quickly join the edges of a wound in tissue without threading and tying numerous individual stitches. The new suture methods are performed in a manner similar to conventional suturing thus realizing the advantages thereof. The methods minimize damage to tissue when inserted and minimize scarring or tissue necrosis across the wound. The sutures can be placed in the tissue in a manner to control and adjust the tension on the suture or the compression of the tissue.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the methods of the present invention can be used alone or with other closure methods, such as topical skin adhesives to aid in holding the position of the tissue. Accordingly, we intend to cover all such modifications, omission, additions and equivalents as may be included within the spirit and scope of the invention as defined by the following claims.

What is claimed is:

1. A method of mounting a device to an internal organ of a subject, the device including at least one eyelet for securing the device and through which a suture may pass, using a barbed suture including an elongated body, first and second sharp pointed distal ends for penetrating tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end, the method comprising the steps of: (a) placing the device in a desired position on an internal organ of the subject's body, where the internal organ is selected from liver, gall bladder, bowel and stomach; (b) threading-the first pointed end of the suture through one eyelet; (c) inserting the first pointed end of the suture into tissue of the internal organ; (d) pushing the first end of the suture through the tissue until the first end of the suture extends out of the tissue at an exit point; (e) gripping the first end of the suture and pulling the first end out of the tissue while drawing the first portion of the suture through the tissue, leaving a portion of the suture between the first and second axial locations out of the tissue and leaving a length of the first portion of the suture in the tissue between the point of insertion and exit point of the first end; (f) after steps (a)-(e), inserting the second pointed end of the suture into tissue of the internal organ; (g) pushing the second end of the suture through the tissue until the second end of the suture extends out of the tissue at an exit point, leaving a portion of the suture between the first and second axial locations out of the tissue; and (h) gripping the second end of the suture and pulling the second end out of the tissue while drawing the second portion of the suture through the tissue until the device is mounted on the internal organ of the subject's body, and leaving a length of the second portion of the suture in the tissue of the internal organ between the point of insertion and exit point of the second end; wherein the first and second portions of the suture extend in the tissue in generally opposing directions and cause the suture to resist displacement of the device away from the internal organ.

2. The method of claim 1 wherein at least one of the first and second sutures is inserted in a curvilinear path.

\* \* \* \* \*